US009762565B2

(12) United States Patent
Eilers et al.

(10) Patent No.: US 9,762,565 B2
(45) Date of Patent: Sep. 12, 2017

(54) SPATIAL-LIGHT-MODULATOR-BASED SIGNATURES OF INTRINSIC AND EXTRINSIC SCATTERING SURFACE MARKERS FOR SECURE AUTHENTICATION

(71) Applicants: Hergen Eilers, Spokane, WA (US); Benjamin Richard Anderson, Spokane, WA (US); Ray Gunawidjaja, Spokane, WA (US); Patrick David Price, Spokane, WA (US)

(72) Inventors: Hergen Eilers, Spokane, WA (US); Benjamin Richard Anderson, Spokane, WA (US); Ray Gunawidjaja, Spokane, WA (US); Patrick David Price, Spokane, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 15/191,964

(22) Filed: Jun. 24, 2016

(65) Prior Publication Data

US 2016/0377423 A1  Dec. 29, 2016

Related U.S. Application Data

(60) Provisional application No. 62/185,065, filed on Jun. 26, 2015.

(51) Int. Cl.
*G06K 9/74* (2006.01)
*H04L 29/06* (2006.01)
*H04L 9/00* (2006.01)
*G01N 21/956* (2006.01)

(52) U.S. Cl.
CPC ............. *H04L 63/08* (2013.01); *H04L 9/00* (2013.01); *G01N 21/95623* (2013.01)

(58) Field of Classification Search
CPC  H04L 63/08; H04L 9/00; G07F 7/086; G07D 7/124; B41M 3/14; G01N 21/95623
See application file for complete search history.

(56) References Cited

U.S. PATENT DOCUMENTS 5,327,286 A * 7/1994 Sampsell ......... G01N 21/95623
                                                  359/559
5,815,597 A * 9/1998 Horner ..................... G06E 1/04
                                                  359/561

(Continued)

*Primary Examiner* — Kara E Geisel
*Assistant Examiner* — Maurice Smith
(74) *Attorney, Agent, or Firm* — Whitham, Curtis & Cook, P.C.

(57) ABSTRACT

Unique methods and systems are introduced herein for the determination of unique spatial light modulator based optical signatures of intrinsic and extrinsic scattering surface markers. These techniques can be used to authenticate semiconductor components and systems at various stages during the manufacturing process by measuring and cross correlating the surface marker's unique optical signature. In addition, these techniques can be used with extrinsic surface markers which are added to existing hardware (e.g. containers, locks, doors, etc.). These markers can then be measured for their unique optical signatures, which can be stored and used at a later time for cross-correlation to authenticate the surface marker and verify the hardware's provenance.

17 Claims, 18 Drawing Sheets

(56) References Cited

U.S. PATENT DOCUMENTS

| | | | | |
|---|---|---|---|---|
| 7,317,814 B2* | 1/2008 | Kostrzewski | ........... | G06E 3/001 356/300 |
| 2002/0044277 A1* | 4/2002 | Yonezawa | ........ | G01N 21/95623 356/237.2 |
| 2009/0180109 A1* | 7/2009 | Ikota | ................ | G01N 21/9501 356/239.3 |
| 2014/0319815 A1* | 10/2014 | Sekine | .................... | B41M 3/14 283/85 |

* cited by examiner

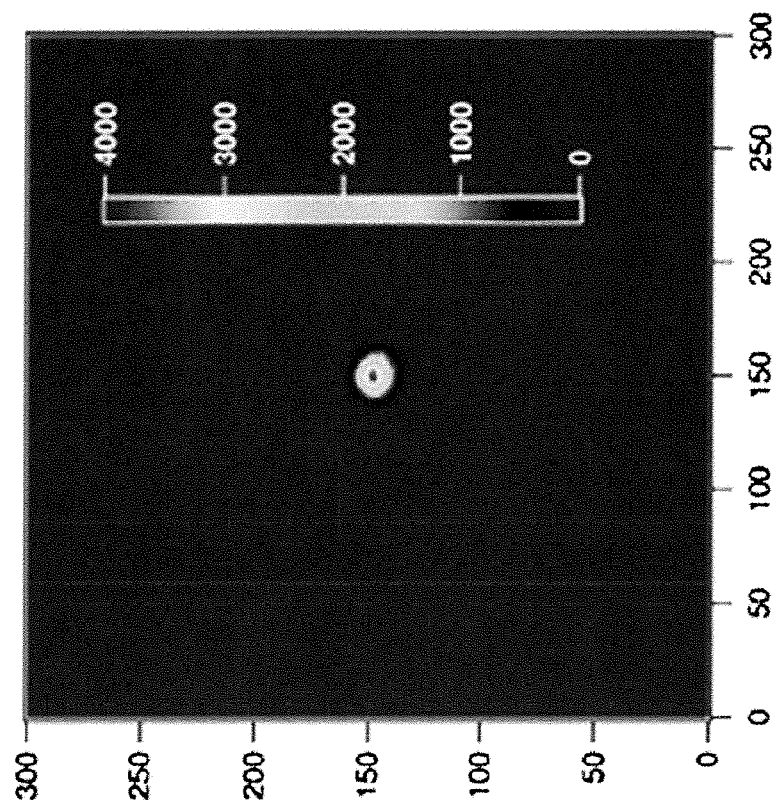
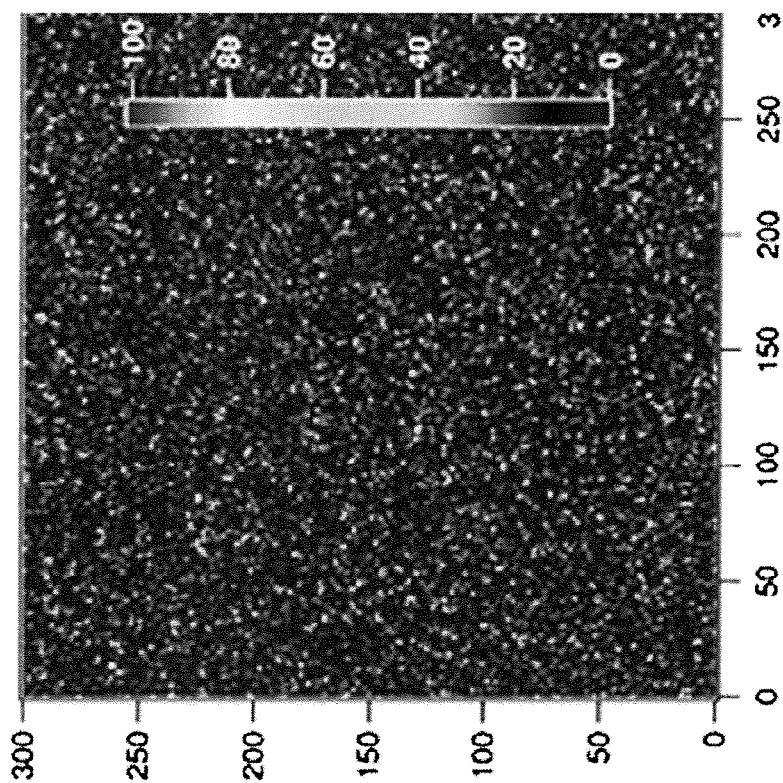
FIG. 2B
FIG. 2A

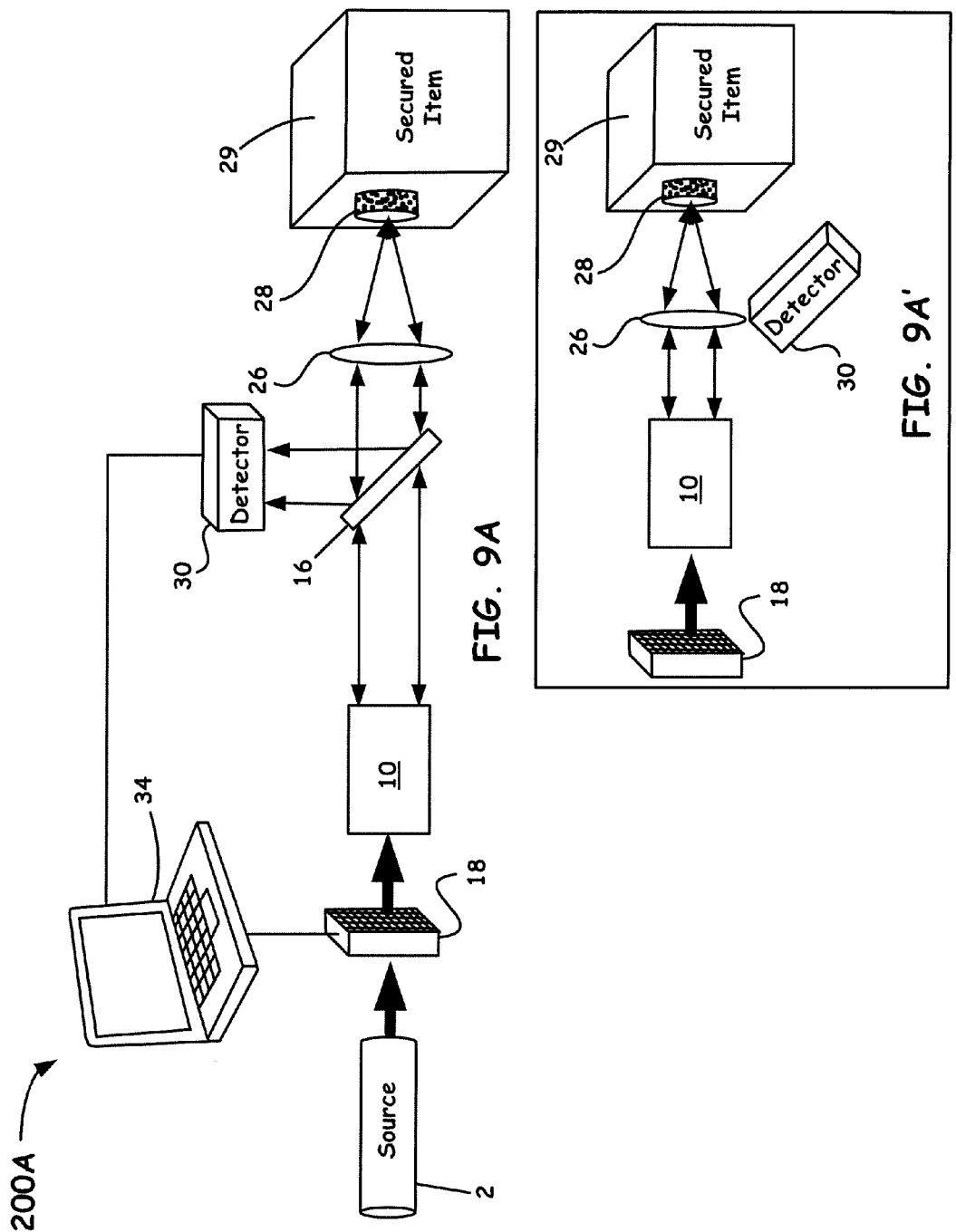

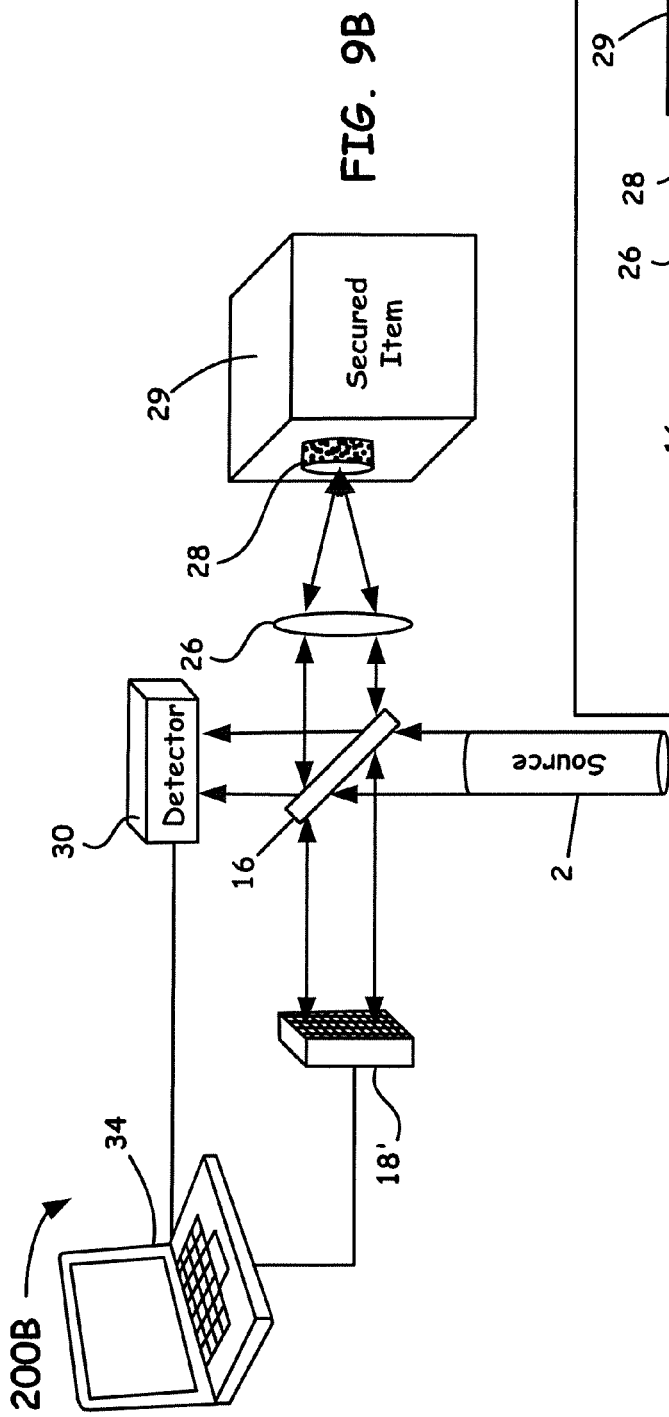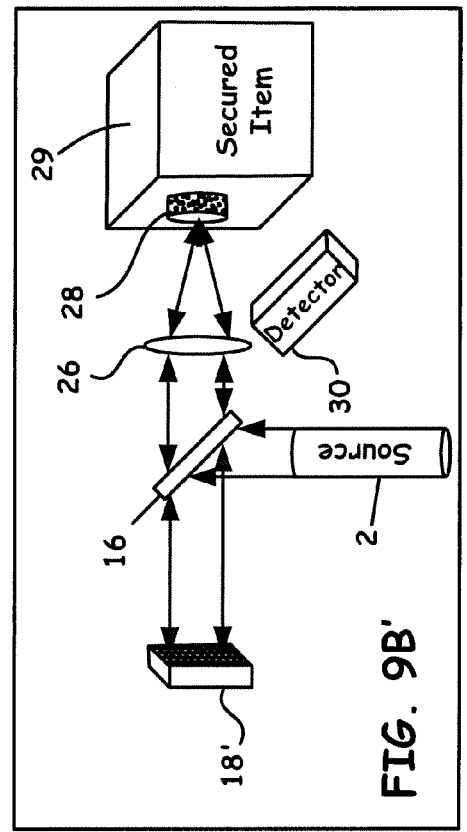

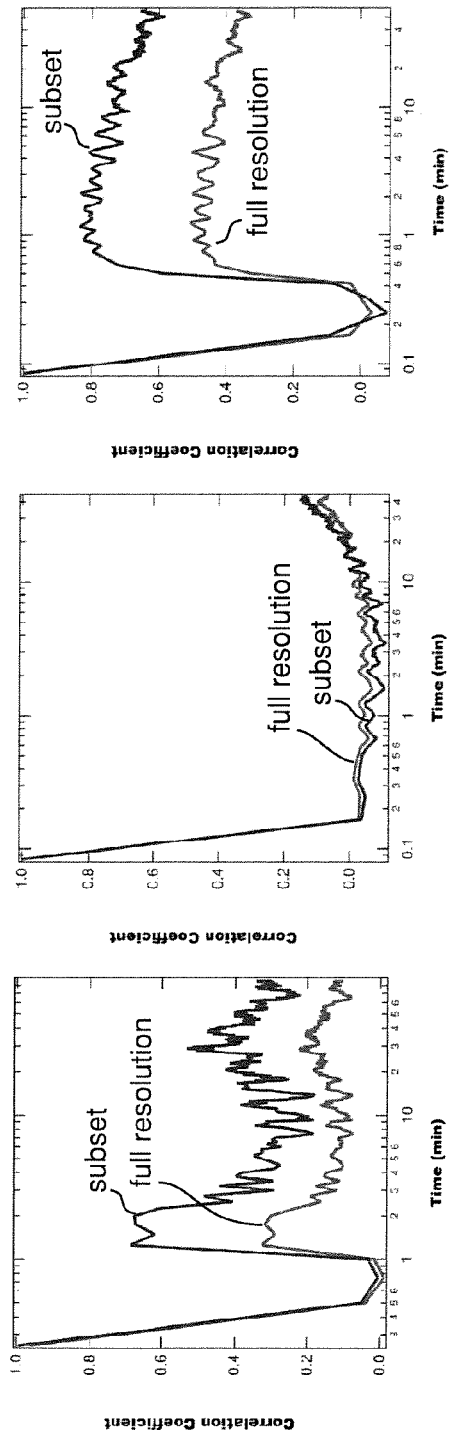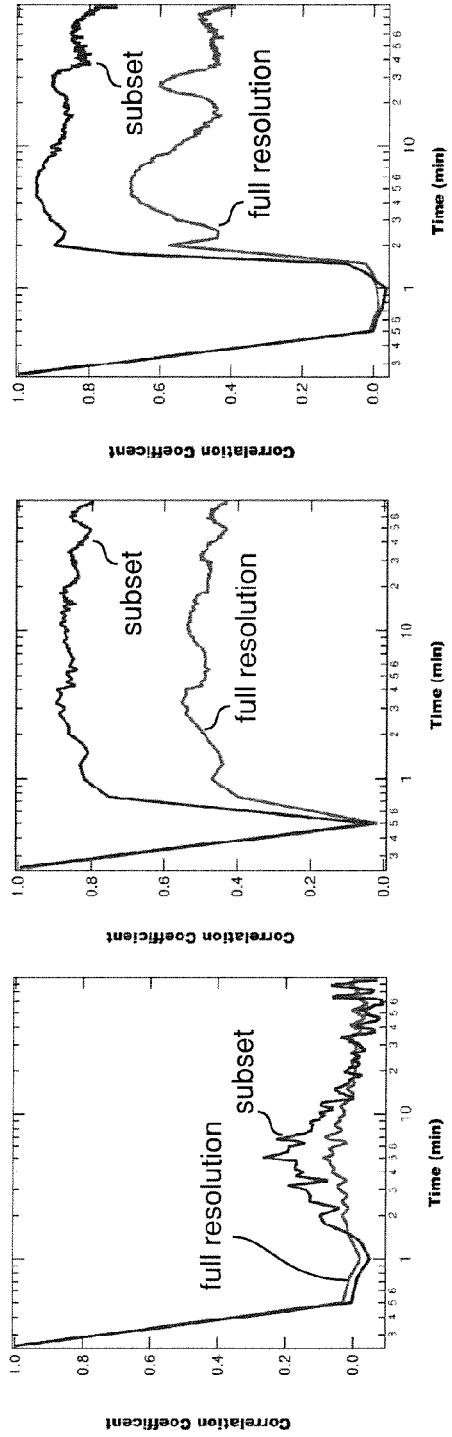

SPATIAL-LIGHT-MODULATOR-BASED SIGNATURES OF INTRINSIC AND EXTRINSIC SCATTERING SURFACE MARKERS FOR SECURE AUTHENTICATION

CROSS-REFERENCE TO RELATED APPLICATIONS

This application claims the benefit of U.S. Provisional Patent Application No. 62/185,065 filed Jun. 26, 2015, the complete contents of which are herein incorporated by reference.

STATEMENT REGARDING FEDERALLY SPONSORED RESEARCH OR DEVELOPMENT

This invention was made with government support under HDTRA1-13-1-0050 awarded by the Defense Threat Reduction Agency. The government has certain rights in this invention.

BACKGROUND OF THE INVENTION

Field of the Invention

The present embodiments herein generally relate to the field of authentication and more particularly, the embodiments herein generally relates to methods and systems for authenticating articles using Spatial-Light-Modulator signatures.

Discussion of the Related Art

Authentication has become an important requirement in today's globally interconnected technological environment. An example of the necessity of secure authentication is the common occurrence of counterfeit—or otherwise unauthorized—goods being manufactured, distributed, and sold in direct competition with authentic goods in the commercial manufacturing world. The semiconductor industry is particularly vulnerable to these types of attacks as the global supply chain provides numerous opportunity for tampering and/or counterfeiting. To combat these types of attacks it is desirable to have a secure method of authentication at each step in the supply chain. Secure authentication requires the use of tamper-indicating devices (i.e., seals or security seals) and integrated systems designed to provide information of unauthorized entry or access into protected areas. In addition to the semiconductor industry, secure authentication has a myriad of other applications ranging from, but not limited to, hazardous waste accountability, security records management, inventory and cargo security, theft prevention and detection, international treaty monitoring, customs, and tamper-evident packaging of consumer products.

While many of the secure authentication's applications are modern, various forms of tamper-indicating devices have been used for hundreds of years with mixed degrees of success (i.e. the ability to indicate unauthorized access). Detailed background information on tamper-indicating devices (e.g., seals) is described in, "Tamper-Indicating Seals," by Roger G. Johnston, Am. Sci. 94 (6), 515-523 (2006). Generally, seals fall into two major categories: passive and active. Passive seals, such as, but not limited to, tamper-evident containers and enclosures, fiber optic bundles that show changes in light transmission when cut, and other devices or components that that show evidence of being opened or showing irreversible damage or changes, work without a power source and are usually inexpensive one time use devices. Active seals, by contrast, are typically powered by electricity, either internally or externally, and are often reusable. Additionally, active seals typically can be interfaced either wirelessly or wired to a host system or network providing real time monitoring of the seals state.

At this point it is important to note that the seal itself, either active or passive, does not generally provide resistance to tampering but only records information that it has occurred. The requirement of traditional seals to store evidence of tampering in a non-erasable manner is one of the fundamental difficulties of secure authentication. One solution to this problem is to use 'anti-evidence' based seals, in which the seals store information that tampering has not occurred. If the seal is tampered with the information is destroyed and its absence indicates tampering.

While anti-evidence seals address the need to store evidence of tampering, they have a vulnerability to counterfeiting, in which an attacker can produce a duplicate seal containing the 'anti-evidence' and merely replace the seal after attacking the original seal. The best defense to counterfeiting attacks is the usage of physically unclonable functions (PUFs). PUFs are physical features embodied in a physical structure that are unfeasibly difficult to reproduce. Some examples of PUFs are: scattering composites, material surface and volume defects, Static RAM (SRAM) devices, and field programmable gate arrays (FPGAs). PUFs typically are interrogated using a challenge/response approach via either electronic or optical means, with optically based systems being called optical PUFs (O-PUFs).

A specific example of an optical PUF implementation is based on measuring the transmissive speckle patterns of scattering tokens added to devices such as credit cards. The 2D speckle pattern is then filtered using a multiscale Gabor transform, resulting in a 1D key. Such a Gabor transform has the following properties: it converts an input of arbitrary length into a fixed-length output; changing one input bit changes about half of the output bits; it is not possible to find an input for a given output; and it is almost impossible for two inputs to have the same output. This key is first measured after the token is manufactured or activated. In a challenge/response approach, whenever the token is used, the speckle pattern is re-measured and the 1D key produced and compared with the original key in the database. Because of the random nature of the token (scattering medium), it is impossible to counterfeit it.

A different O-PUF approach in use is Laser Surface Authentication (LSA), reported by Cowburn in 2008, and commercially pursued by INGENIA Technologies. In this approach, a laser is focused onto an extrinsic scattering marker or intrinsic scattering surface and several detectors at fixed locations measure the intensity of the scattered light. The intensity distribution is then stored in a database for future authentication requests. Assuming the scattering is due to a random distribution of scattering particles in an extrinsic marker, or a random distribution of intrinsic surface defects, the intensity distribution will be unique to the specific surface.

The last specific example of an O-PUF implementation is Laser Speckle Photography (LSP), which has been developed to detect surface tampering. In this approach, a scattering surface is illuminated by a laser projector and a camera records the resultant speckle pattern. The speckle pattern of the pristine surface can then be used to make comparisons to speckle patterns recorded at later times. A change in the speckle pattern compared to the pristine response implies that the surface has been tampered with.

In the specific examples considered above a surface is interrogated by a fixed optical signal. A different, more robust, approach to implementing O-PUFs is to use optical modulation (such as a spatial light modulator or digital-mirror-device) to control the optical response of a surface. In these approaches the modulation pattern becomes part of the challenge/response system adding another layer of complexity, which helps with making the PUF truly unclonable.

Table I below provides an overview of several implementations of optical PUFs. Depending on the specific configuration, a Spatial Light Modulator (SLM) may or may not be required. In all cases, a laser is used for illumination to provide coherent light. CCD arrays are used to measure the responses. There are usually strict alignment requirements, often requiring markers, to ensure that challenges are measured at the same location as the original measurement.

TABLE I

Examples of various O-PUFs.

| Method | Object | SLM | Time for measuring optical signature |
|---|---|---|---|
| 1 Scattering token | Scattering particles in epoxy | N | Fast |
| 2 Linear luminescent token | Luminescent particle in epoxy | Y | Slow |
| 3 Non-Linear 2-Photon token | Luminescent particle in epoxy | Y | Slow |
| 4 Scattering token | Scattering particles in epoxy | Y | Fast |
| 5 Laser surface authentication (LSA) | Intrinsic surface | N | Fast |
| 6 Laser speckle photography (LSP) | Intrinsic surface | N | Fast |

In addition to the basic challenge-response mechanism of the above listed O-PUFs other techniques have been developed to help enhance their reliability and security. For instance, in 2005, Skoric et al. described the use of polarizing elements to reduce effects from surface scratches or dirt, an application of a Gabor transform to extract bit strings from speckle patterns, and error correcting codes to help reduce false positives. As another example, in 2013, Goorden et al. made major improvements in the security of O-PUFs using quantum secure authentication (QSA). QSA uses low photon numbers and entangled photons to protect against "man-in-the-middle" attacks, as such attacks would change the quantum states of the photons, indicating an attack.

All of the above mentioned techniques are designed to try and address the modern requirements of secure authentication. A successful secure authentication technique needs to unambiguously indicate that tampering and/or counterfeiting has occurred, be resistant to false positives, and be of a degree of complexity making counterfeiting unfeasibly difficult. The novel embodiments of the present invention is directed to such a need.

SUMMARY OF THE INVENTION

It is to be appreciated that the present example embodiments herein are directed to an authentication system that includes: an optical source of radiation; a spatial light modulator (SLM) configured to modulate a wavefront of the optical source of radiation; one or more optical components configured to use the modulated wavefront so as to provide an optical source of radiation challenge to at least one of: the surface of a sample and within a desired volume in the bulk of the sample; a detector configured to analyze an induced optical response by the sample as a result of being illuminated with the optical source of radiation challenge; and a controller coupled to the SLM and configured to cooperatively operate on a closed feedback loop to optimize the detection of the induced optical response by varying in an iterative manner, one SLM system parameter selected from: an SLM bin size (b), a number of SLM phase steps (M), an active SLM area (L2), a detector integration radius (r), and an on-sample beam spot size (w), while holding all other of the parameters fixed so as to optimize the authentication system for subsequent measurements of the intensity enhancement or optical pattern of the induced optical response by the surface marker.

Another aspect of the present embodiments is directed to an authentication method, that includes: providing an optical source of radiation; modulating a wavefront of the optical source of radiation; utilizing the modulated wavefront to provide an optical source of radiation challenge to at least one of: the surface of a sample and the volume in the bulk of the sample so as to induce an optical response; monitoring the optical response from the sample; optimizing the authentication process by varying in an iterative manner, one SLM system parameter selected from: an SLM bin size (b), a number of SLM phase steps (M), an active SLM area ($L^2$), a detector integration radius (r), and an on-sample beam spot size (w), while holding all other of the parameters fixed; and analyzing and optimizing the induced optical response from the sample as a result of being illuminated with the optical source of radiation challenge.

Accordingly the methods and systems disclosed herein can enable, as one example embodiment, the measuring of optical signatures of semiconductor components and systems at various stages during the manufacturing process, and then to re-measure these signatures at a later time for subsequent cross-correlation to authenticate the measured part and verify its provenance. In addition, the methods and systems disclosed herein can use unique optical surface markers attached to hardware to be subsequently optically interrogated for their unique signatures, which can be re-measured at a later time to authenticate their provenance.

BRIEF DESCRIPTION OF THE DRAWINGS

FIG. 2A shows a random distribution of scattered light before optimization.

FIG. 2B illustrates an example of the intensity profile after optimization.

FIG. 9A shows another general example reflection geometry embodiment of an "on-site" transmissive spatial-light-modulator-based authenticating system to characterize signatures of scattering composites and/or original object features.

FIG. 9A' shows another general example reflection geometry embodiment of an "on-site" transmissive spatial-light-modulator-based authenticating system to characterize signatures of scattering composites and/or original object features but with an off-axis detector arrangement.

FIG. 9B shows another general example reflection geometry embodiment of an "on-site" reflective spatial-light-modulator-based authenticating system to characterize signatures of scattering composites and/or original object features.

FIG. 9B' shows another general example reflection geometry embodiment of an "on-site" reflective spatial-light-modulator-based authenticating system to characterize signatures of scattering composites and/or original object features but with an off-axis detector arrangement.

FIG. 13A shows correlation coefficient as a function of time after tampering flexible PU with methanol.

FIG. 13B shows correlation coefficient as a function of time after tampering flexible PU with acetone.

FIG. 13C shows correlation coefficient as a function of time after tampering flexible PU with propanol.

FIG. 13D shows correlation coefficient as a function of time after tampering rigid PU with methanol.

FIG. 13E shows correlation coefficient as a function of time after tampering rigid PU with acetone.

FIG. 13F shows correlation coefficient as a function of time after tampering rigid PU with propanol.

DETAILED DESCRIPTION

Figure 1A:
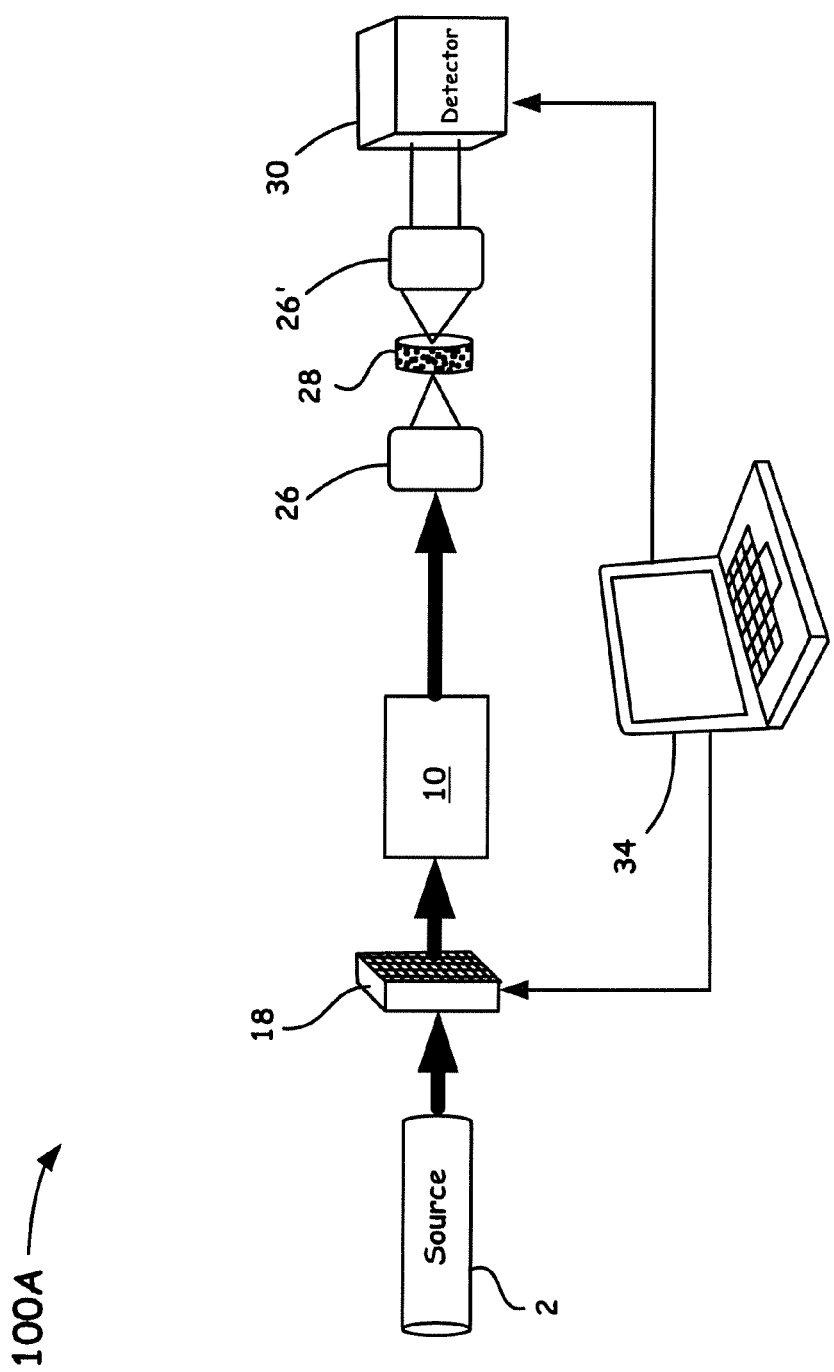
FIG. 1A shows a general example transmission geometry embodiment of a transmissive spatial-light-modulator-based authenticating system to characterize signatures of surface markers and/or original object features.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. It is to be noted that as used herein, the term "adjacent" does not require immediate adjacency. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise.

In addition, unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

The configurations and methods herein are utilized to evaluate surface and volume optical responses of PUFs, which include intrinsic hardware properties, such as defects, and extrinsic surface markers, such as adhesives filled with scattering particles and adhesives filled with scattering particles and/or optically-active particles and/or molecules (e.g. organic and inorganic dyes, rare earth doped particles). Example organic particles utilized herein include sucrose, acetaminophen, anthracene, and tetracene. Example optically-active particles utilized herein include Rhodamines, Coumarines, Anthraquinones, Exalites, lanthanide-containing dyads. Optical PUFs are generally opaque media, which when illuminated by optical sources disclosed herein, have a unique optical response, such as, but not limited to: speckle pattern, transmission, lasing spectrum, fluorescence spectrum, pulse compression, two-photon fluorescence spectrum, two-photon absorption spectrum, etc.

In particular with respect to the use of extrinsic surface markers, the distribution of scattering particles can be accomplished using in-house prepared or commercially available powders (such as $TiO_2$, $ZnO$, $ZrO_2$, $Y_2O_3$, $SiO_2$, $Ag$, $Au$, etc.) combined with a solid matrix, such as polymer adhesives (e.g. urethanes, epoxies, resins, cyanoacrylates, and methacrylates), sol-gels, aero-gels, and glasses. The powders are often mixed directly into the solid matrices to create composites. Surface functionalization of the powders may be performed to prevent agglomeration and improve homogeneity.

In general, the techniques and systems described herein are directed to the verification (authentication) of intrinsic and/or extrinsic surface markers (with extrinsic surface markers briefly described above) that can desirably be utilized as tamper-proof seals that are unclonable. These intrinsic and/or extrinsic surface markers are therefore optical PUFs, as they utilize large degrees of freedom in order to make counterfeiting nearly impossible. The value of using such a PUF is that they can be utilized as unique physical authenticators, (i.e., components that cannot be reproduced identically), as they contain large numbers of randomly distributed particles and/or defects in the scattering volume, making it impossible to recreate the PUF such that the optical response to an optical challenge is identical.

For example, an extrinsic surface marker can be added to the product at an early stage and stay with it throughout the manufacturing process and beyond. As long as its surface is accessible to an optical interrogation process, it can in principle be measured at any time, for as long as subsequent processing steps do not alter the surface of the marker. Such an extrinsic method can even be further divided into a passive preferred methodology (e.g., scattering particles) and an active methodology (e.g., locating one or more luminescent particles in a scattering volume or by measuring the random lasing spectrum of the marker after being optically pumped). The benefit of an extrinsic methods is the use of well characterized surface marker. In particular, while no optical signature from any two surface markers are identical, all the optical signatures nonetheless have similar characteristics.

It is to be noted, however, that while the PUFs described immediately above relate to a desirable extrinsic method of providing a surface marker (e.g., a component having scattering particles) added to hardware or components that have been or can be optically investigated to determine its unique optical fingerprint, the embodiments herein are not solely limited to just those configurations.

For example, the embodiments herein can also be utilized in an "intrinsic" method of authentication that is directed to optically measuring the fingerprints of the actual component (e.g., a semiconductor component) or design hardware (e.g., Si surface, SiO2 surface, packaging material surface, circuit design map, etc.) without departing from the scope of the present application disclosed herein. Such a methodology is beneficial in that no surface markers are needed and no changes to the manufacturing process need to occur despite the potential for different optical responses resulting from, for example, differences in surface morphologies.

Specifically, the intrinsic track focuses on optically measuring the fingerprints of the actual hardware components, be they circuit layout maps, processed wafer, packaged chips, or populated circuit boards. For example a semiconductor wafer surface can be measured early in the manufacturing process and, if desired, authenticated along the manufacturing process until the chip is finally packaged. At that time, a signature of the packaging material can be measured to associate a particular chip with a particular packaging. If desired, a signature of the surface of the chip can be measured at various stages. Once the chip is packaged and its signature measured, the signature is entered into a database for later verification purposes. A customer can either be given access to the database and then measure the signature of the part at the customer location, or the customer can provide access to the part through a fiber-optical connection, allowing the manufacturer or an authorized third party to perform the authentication remotely. For increased security, Quantum-Secure Authentication (QSA), as discussed herein below, can additionally be employed under those circumstances.

Measuring optical signatures on surfaces for provenance authentication, requires that the two measurements—original and follow-up—are measured on the same surface. Whenever a surface is completed, and the product needs to be moved, shipped, or otherwise transported or stored, an optical signature can be measured and used for later authentication of the product. For example, during semiconductor processing this could include authentication at different stages including: silicon wafer finishing, wafer probe testing, chip separation, visual inspection, and packaging.

It is to be appreciated that the authentication embodiments herein utilize spatial light modulation (SLM) as a desirable technique to enable phase and/or amplitude modulation of wave fronts. As known to those of ordinary skill in the art, such spatial light modulators are configured as arrays of pixels that are adjustable. When, for example, a laser beam is directed onto such an SLM, individual phase and amplitude parts of the reflected or transmitted laser beam can be adjusted/modulated when combined using feedback from, for example, a well-positioned array detector.

In particular, the authentication techniques provided herein use such computer-controlled spatial light modulators (SLM) with the aforementioned feedback loop so as to shape the phase and/or amplitude of a beam of coherent electromagnetic radiation incident on a sample so as to control the induced optical response of the sample.

It is to be noted that as used herein for any of the configurations disclosed, the initial directed beam to a sample and/or one or more phase and/or amplitude modulated beams operating as a stimulus to the sample is deemed a "challenge" and the resulting radiation from the sample due to the challenge is deemed an optical "response" that is dependent in a complex way on the challenge and the details of the surface/volume features of an object or a PUF's configured diffusive structure. Thus, as used herein, the challenge and the response is called a "Challenge-Response".

The detector, such as but not limited to, a photodiode, a spectrometer, but more often an array detector to include but not limited to charge coupled devices (CCD's), charge injection devices (CID's), and complementary metal-oxide-semiconductor (CMOS) arrays are thus placed in a manner to monitor the samples optical response as the pixels of the SLM are phase tuned.

A prototype system and samples were put through a variety of tests. The tests include characterizing the influence of experimental parameters on the enhancement, the influence of sample properties on the enhancement, and the system's sensitivity to changes in positioning. Ten different polymers' thermal, UV, and ionizing radiation stability were also characterized. Clear Flex 95 (flexible) and Crystal Clear 202 (rigid) which are polyurethanes were determined to be suitable candidates for field applications in a nuclear facility. With the polymer host chosen, preliminary, rudimentary tamper-indication tests were performed utilizing crude tampering attacks such as: brute force lifting, deformation (poking), heating, and solvent-based attacks. From the various tampering tests, it's found that both NP-polymer composites display strong tamper-indicating ability.

Specific Description

Figure 1B:
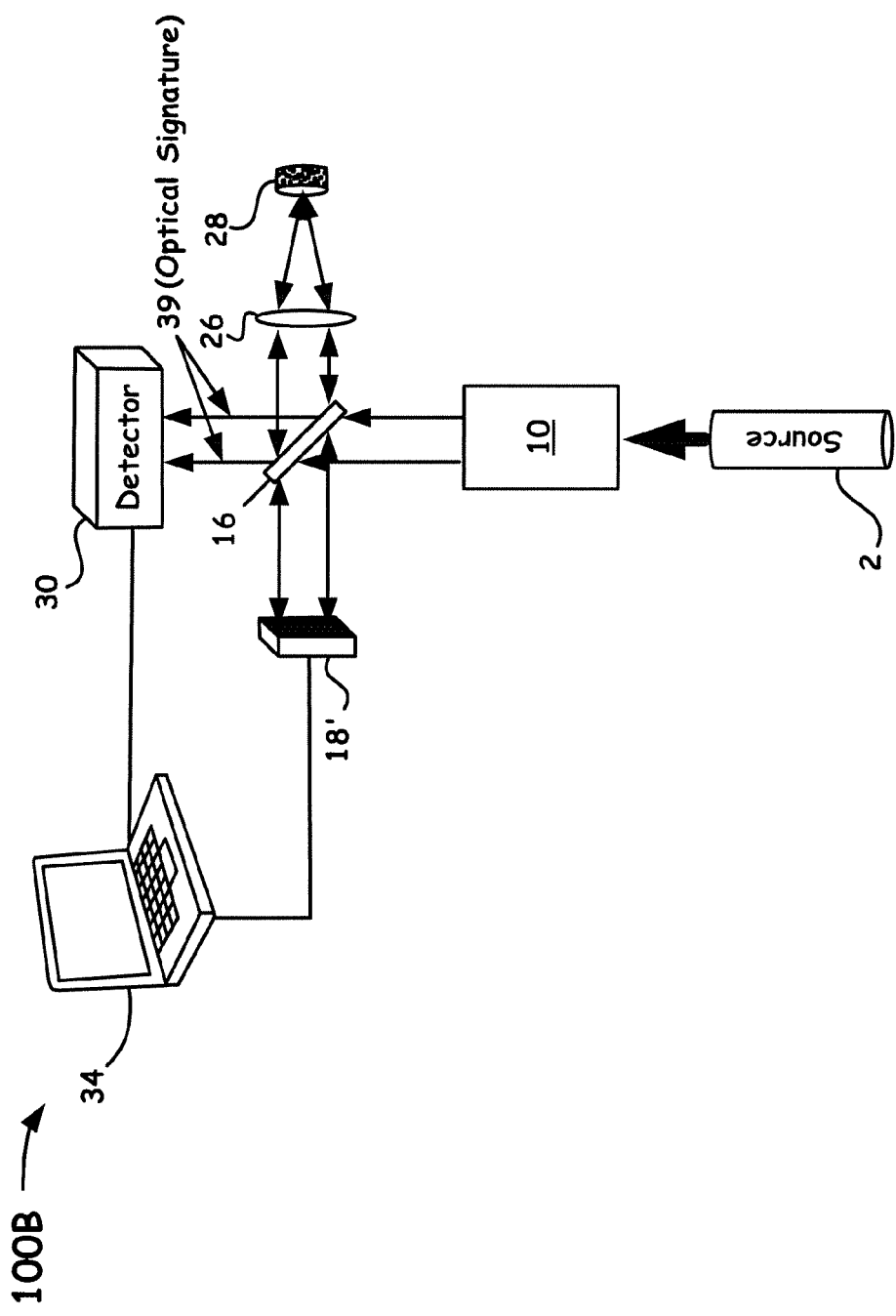
FIG. 1B shows a general example transmission geometry embodiment of a reflective spatial-light-modulator-based authenticating system to characterize signatures of surface markers and/or original object features.

As non-limiting examples of the invention, FIG. 1A and FIG. 1B show embodiments of a system of authentication as constructed in accordance with the teachings herein. The system as specifically shown in FIG. 1A and designated generally by the reference numeral 100A, is shown as a transmission method and configuration to illustrate the principles herein for optically characterizing as well as authenticating, for example, a given configured scattering composite (e.g. scattering particle-doped polymer or polymer doped with scattering particles and optically active particles), to be utilized as a unique surface marker (e.g., tamper proof seal). It is to be noted that while the system 100A of FIG. 1A is beneficial for illustrative purposes of a transmittance geometry, it is to be understood that other alternative configurations (geometries) to provide alternative authentication methodologies—such as, but not limited to: a reflectance geometry (e.g., system 100B as shown in FIG. 1B), one- and two-photon fluorescence geometries, a two photon absorption geometry, a random (RL) lasing geometry, a four-wave mixing geometry, a magneto-optical effects geometry, an electro-optic effects geometry, a mechano-optics geometry, a thermo-optics geometry, and other geometries utilized and understood by those of ordinary skill in the art can be incorporated, as to be discussed in more detail herein.

System 100A, as shown in FIG. 1A and system 100B, as shown in FIG. 1B, contain the following basic components: an electromagnetic source optical radiation 2, an electrically- or optically-addressed transmissive 18 or reflective spatial light modulator (SLM) 18' (e.g. Liquid crystal on silicon (LCOS), digital mirror device (DMD)), control electronics (e.g. computer) 34, a sample (surface marker, seal) 28, a detector 30, and optics for beam shaping, polarization control, and beam directing. Thus, it is to be noted that while the basic components are utilized, the system 100A of FIG. 1A shows an example geometry for a transmissive SLM 18 and the system 100B of FIG. 1B shows an example geometry for a reflective SLM 18'.

It is also to be noted that while FIG. 1A and FIG. 1B show the processor 34 generally depicted as a laptop computer, it is to be emphasized that the operation of components within system 100 or any other embodiment disclosed herein can equally be enabled by a controller and data system of various circuitry of a known type. Such a control and data system can thus be in the form of a desktop computer or a laptop computer as shown in FIG. 1A and FIG. 1B, or can be implemented by any one of or a combination of general or special-purpose processors (digital signal processor (DSP)), firmware, software, and/or hardware circuitry to provide instrument control, data analysis, etc., for the example configurations disclosed herein.

In operation, the source directs light (as denoted by large arrow) towards the SLM 18, 18', as shown in FIG. 1A and FIG. 1B, either directly or reflected by optical means known in the art, such as, but not limited to, a beamsplitter 16, as shown in FIG. 1B. The source 2 itself is configured to enable coherent emission. Desirable sources 2 include, but are not strictly limited to, diode lasers, Diode pumped Solid State lasers (DPSS) lasers, frequency doubled, tripled, and quadrupled diode lasers, superluminescent LEDs, solid-state lasers, frequency doubled, tripled, and quadrupled diode solid-state lasers, gas lasers, optical parametric amplifiers, etc., and/or any coherent optical source that can provide the required wavelengths and intensities so as to conform to the workings of the examples embodiments herein.

The light beam is then often conditioned (e.g. expanded, spatially filtered, polarization fixed, etc.) using appropriate optics, as generally referenced by the numeral 10, and then it is either transmitted through a transmissive SLM 18 (FIG. 1A) or reflected from the SLM 18', as shown in FIG. 1B, which modulate the beam's amplitude and/or phase. The modulated beam is then focused onto the sample using a lens or lens system.

Turning in particular to the system 100 of FIG. 1A, after propagating through the opaque sample, the scattered light is collected by another lens or lens system, e.g., 26', which collimates the light onto a detector 30. It is to be noted that while the authenticating transmission system 100 of FIG. 1A shows a pair of objectives (e.g., 26, 26' lenses), the system shown therein is not limited to such an arrangement as single lens systems to focus the beam through the sample 28 or complex combinations of lenses known in the art (e.g., before and after the sample 28) can also be utilized when conforming to the authenticating demands required.

Turning now in particular to the system 100B of FIG. 1B, after being reflected from the SLM 18' the modulated light is directed back through the beamsplitter 16 and focused via lens or lens system 26 onto the opaque sample 28. The scattered light is then collected by the lens or lens system, e.g., 26, which operates by its configuration to collimate the light having the optical signature 39. The light having the optical signature 39 is then directed by the beamsplitter 16 onto a detector 30.

As to be appreciated by those of ordinary skill in the art, the SLM 18, 18' and a detector 30 (e.g., an array detector) operate on a closed feedback loop using an optimization algorithm (such as an iterative, standard genetic, microgenetic, or partitioning, etc.). In particular, since there is no a priori knowledge of the scattering properties of a media (e.g., sample 28), a computer-controlled spatial light modulator (SLM) 18, 18' with a feedback loop can be used to shape the incoming laser source 2 beam in such a manner that the light propagating through the sample produces a desired optical response (such as, but not limited to: focal spot, fixed intensity pattern, desired fluorescence or random lasing spectrum, polarization rotation, etc.).

Detectors 18 that are applicable to the configurations herein can, if the configuration warrants, be a spectrometer, photodiode, avalanche photodiode, photomultiplier tube (PMT), a Charge Coupled Device (CCD), a CMOS array, a Charge Injection Device (CID) detector, an avalanche CCD photo-detector, area sensors with an image intensifier, or EMCCD (Electron Multiplying CCD). Without limiting to just the above devices however, it is to be understood that any device capable of measuring the optical response (e.g. speckle pattern, light intensity, fluorescence spectrum, random lasing spectrum) of the sample 28 can be used for the configurations disclosed herein.

The sample's optical response (measured by the detector) is a function of scattering within the bulk volume and/or surface of the sample and the incident wavefront. By varying the wavefront's phase and/or amplitude using the SLM 18, 18' and an optimization algorithm (i.e. iterative, standard genetic, microgenetic, or partitioning) the sample's optical response can be tuned to produce a target response (e.g. focal point, lasing spectrum) which is measured by the detector 30. The optimized wavefront producing the target response is then stored in memory as a wavefront "challenge" and the sample's optical response is stored in memory as the specific system "response".

With the sample's challenge-response pair recorded, the information can be used at a later time to authenticate the sample. Authentication occurs when the sample is interrogated with the wavefront determined from the optimization procedure and its response is recorded and compared to the original response. A change in the optical response to the optimized wavefront indicates tampering (either intentional or unintentional).

As an example of this authentication procedure, FIG. 2A shows a sample's transmitted speckle pattern due to a random phase front, while FIG. 2B shows the response to the optimal wavefront. For a non-optimal wavefront the sample's speckle pattern is random and diffuse, while the optimal wavefront produces a tightly focused spot. Using either the wrong wavefront or a tampered sample will result in the speckle pattern, not the expected focused spot.

It is to be noted that the samples used in the example transmission system of FIG. 1A, which produce the patterns shown in FIG. 2A and FIG. 2B, comprise of $ZrO_2$ particles embedded in a polyurethane matrix. While this specific sample configuration was used as an example, the technique described in FIG. 1A is more general and can work with different extrinsic surface markers as well as intrinsic scattering surfaces. Other possible extrinsic surface markers can use other scattering particles (such as, but not limited to: $Y_2O_3$, $TiO_2$, $ZnO$, $SiO_2$), other solid matrices (such as, but not limited to: sol-gels, aerogels, glasses, poly(methylmethacrylate), optically active materials (Eu-doped $ZrO_2$, Rhodamine 6G, Disperse Orange 11), electro-optic materials (e.g. lithium niobate, gallium arsenide, barium borate), and magneto-optic materials (e.g. terbium gallium garnet).

In order to best use optimal wavefront shaping (as done by the disclosures within) to control the unique optical signatures of optical PUFs it is beneficial to understand how different experimental parameters affect the systems operation. The system's optimization dependence is based on five different system parameters: SLM bin size, b, number of SLM phase steps, M, active SLM area, $L^2$, detector integration radius, r, and the on-sample beam spot size, w. Alternative or additional system parameters may also be used in different embodiments.

For comparing the influence of the different variables on optimization one calculates/measures the intensity enhancement, which is defined as shown in Equation 1:

$$\eta \equiv \frac{I}{\langle I_0 \rangle}, \quad (1)$$

where I is the average intensity in the target spot after optimization and $\langle I_0 \rangle$ is the ensemble averaged intensity in the target before optimization. Referring back to FIG. 2A and FIG. 2B, by calculating the average intensity in the spot before and after optimization, the enhancement can be calculated using Equation 1.

Model and Theory

Optimization of transmission/reflection can be described by a model of Gaussian beam propagation where the initial Gaussian electric field has a random phase front due to scattering through/from the sample. This model is known as the random phase Gaussian beam model (RPGBM). The RPGBM begins by assuming a $TEM_{00}$ Gaussian beam is incident on the sample, with the beam waist located at the incident surface. The electric field incident on the sample is therefore given by Equation 2:

$$E_i(x,y) = E_0 e^{-(x^2+y^2)/\sigma_0^2} \quad (2)$$

where $E_0$ is the incident field strength and $\sigma_0$ is the beam's Gaussian width. Scattering through/from the sample in the RPGBM is modeled by the beam width increasing, $\sigma_0 \to \sigma$, and the introduction of a random phase profile, $\Phi(x, y)$. With these transformations the field exiting the sample is given by Equation 3:

$$E(x,y) = E_0 e^{-(x^2+y^2)/\sigma^2 - i\Phi(x,y)}. \quad (3)$$

Assuming that the distance from sample to detector, Z, is much greater than the beam width, $\sigma \ll Z$, we can use Fraunhoffer diffraction theory to determine the beamprofile at the detector. In Fraunhoffer diffraction theory the electric field in the detector plane, $E_d(x' y')$, is given by Equation 4:

$$E_d(x', y') = \int_{-\infty}^{\infty}\int_{-\infty}^{\infty} dx\, dy\, E_0 \exp\left\{-\frac{(x^2+y^2)}{\sigma^2} - i\Phi(x,y) + i\frac{k}{Z}(xx' + yy')\right\}, \quad (4)$$

where k is the wavenumber given by $k=2\pi/\lambda$, with $\lambda$ being the wavelength of light. From the diffracted electric field we calculate the beam's intensity profile given by Equation 5:

$$I_d(x',y') = |E_d(x',y')|^2. \quad (5)$$

The optimization process is then modeled by introducing a phase shift, $\psi(x, y)$, to the beam in the sample plane, where $\psi(x, y)$ represents the influence of SLM phase modulation. With the addition of the SLM phase shift, the field in the detector plane becomes Equation 6:

$$E_d(x', y') = \int_{-\infty}^{\infty}\int_{-\infty}^{\infty} dx\, dy\, E_0 \exp \quad (6)$$
$$\left\{-\frac{(x^2+y^2)}{\sigma^2} - i\Phi(x,y) + i\frac{k}{Z}(xx' + yy') + i\psi(x,y)\right\}.$$

Optimization is therefore modeled by systematically varying $\psi(x, y)$ using an optimization algorithm such that the intensity in the detector plane, given by Equations 6 and 5, produces a tight focused spot of diameter r.

While Equation 6 uses continuous Fourier Transforms, in reality computations are performed on a discrete grid using discrete Fourier Transforms (DFTs). Discretizing Equation 6 gives Equation 7:

$$E_{d;n'm'} = \sum_{n=0}^{N-1} \sum_{m=0}^{N-1} E_0 \exp \left\{ -\frac{(n^2+m^2)\Delta x^2}{\sigma^2} - i\Phi_{n,m} + i\frac{2\pi}{N}(nn' + mm') + i\psi_{n,m} \right\}. \quad (7)$$

where the x, y coordinates are substituted with integer values n, m such that:

$$x = n\Delta x \quad x' = n'\Delta x'$$

$$y = m\Delta x \quad y' = m'\Delta x'$$

with $\Delta x$ being the grid spacing in the sample plane and $\Delta x'$ is the grid spacing in the target plane given by Equation 8:

$$\Delta x' = \frac{2\pi Z}{Nk\Delta x}. \quad (8)$$

Note that Equation 8 implies an inverse relationship between distances in the sample and detector planes.

Computational Details

To determine the effects of the five different system parameters on the optimization of transmission/reflection a 1000×1000 grid is defined with an isotropic grid spacing of $\Delta x$, such that $\Delta x \ll \sigma$, where $\sigma$ is the Gaussian width of the electric field. Using a random number generator each grid point is assigned a phase value between 0 and $2\pi$ with the generated numbers having a uniform probability distribution. The combination of the phase value, $\Phi_{n,m}$, and Gaussian width, $\sigma$ defines the electric field at the sample plane given by Equation 9:

$$E_{n,m} = \sqrt{\frac{2\Delta x^2}{\pi \sigma^2}} \exp\left\{ -\frac{(n^2+m^2)\Delta x^2}{\sigma^2} - i(\Phi_{n,m} - \psi_{n,m}) \right\} \quad (9)$$

where $\psi_{n,m}$ comes from the SLM modulation and the peak field is defined as Equation 10:

$$E_0 = \sqrt{\frac{2\Delta x^2}{\pi \sigma^2}}, \quad (10)$$

such that the total integrated intensity is unity.

Using the sample-plane electric field from Equation 9, optimization is modeled as follows:
1) $\psi_{n,m}$ is varied according to the chosen optimization algorithm and parameters. In this example we use a sequential bin-by-bin optimization method in which one bin is modulated at a time to find the optimal phase value, after which that phase is fixed for that bin.
2) Given $\psi_{n,m}$, $E_{d;n',m'}$ is calculated by taking the DFT of $E_{n,m}$.
3) The intensity is found using $E_{d;n',m'}$ and Equation 5 and the average intensity, $\langle I \rangle$, in a target area of radius r is calculated.
4) A random number, $\sigma_f$, which represents detector noise, is added to the calculated average intensity with the random numbers having an average magnitude of $\langle \sigma_f \rangle = \sqrt{\langle I \rangle}$
5) The intensity with noise term, $\langle I \rangle + \sigma_f$, is then used as the feedback signal for the optimization algorithm.

While an example sequential bin-by-bin optimization algorithm is described herein, the model's optimization steps can easily be adapted for more complex algorithms, such as partitioning and genetic optimization.

Model Results

Bin Size

For modeling the effect of bin size, b, on optimization the following parameters are used: an integration radius of $2\Delta x'$ and three different numbers of phase steps, $M = \{2, 3, 20\}$, and an active side length of $L = 1000 \Delta x$. The calculations are performed both with and without noise with the result that the enhancement as a function of bin size depends on whether noise is present or not.

Figure 3B:
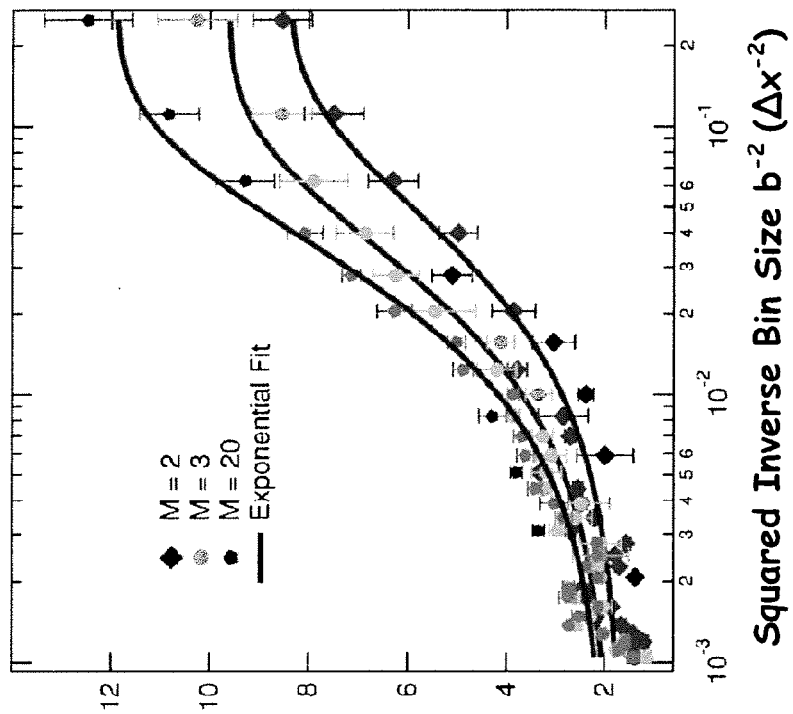
FIG. 3B shows modeled intensity enhancement as a function of inverse squared bin spacing for different M values. The enhancement follows an exponential function with the amplitude changing with M while the shape parameter remains constant.
Figure 3A:
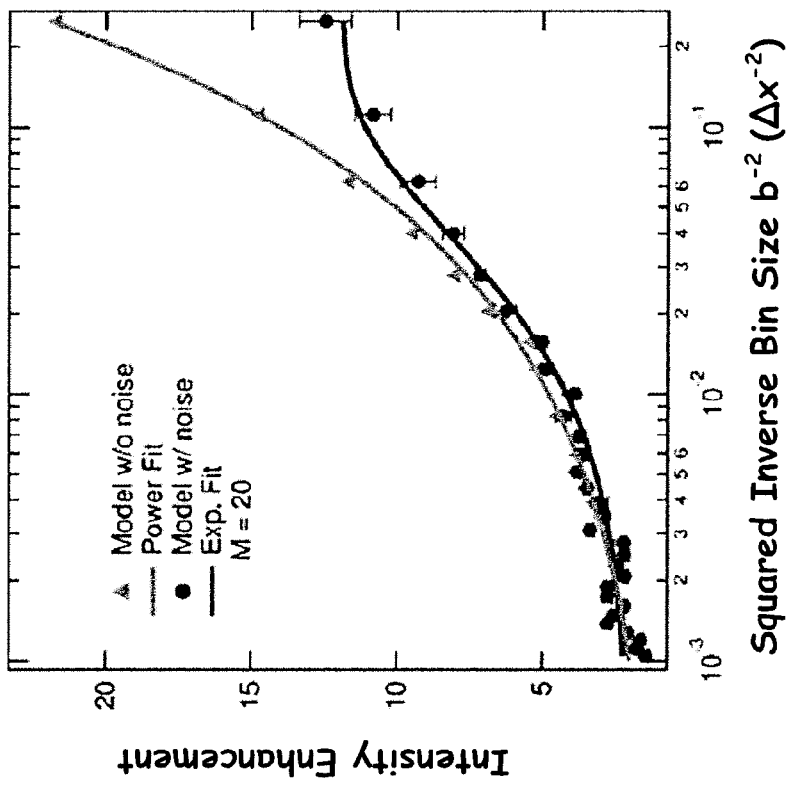
FIG. 3A shows modeled intensity enhancement as a function of inverse squared bin spacing. Without noise the enhancement follows a power function, while with noise the enhancement behaves as an exponential.

To demonstrate the noise dependence FIG. 3A shows a comparison of the enhancement as a function of inverse squared bin size for a calculation with and without noise. Without noise, the intensity enhancement is found to be proportional to a power function $b^{-2p}$ where $p<1$. However, when including noise in the calculation, the intensity enhancement is found to follow an exponential function given by Equation 11:

$$\eta = 1 + \eta_0 \exp\left\{-\left(\frac{ab_0}{b}\right)^2\right\}, \quad (11)$$

where $1+\eta_0$ is the asymptotic enhancement and $\alpha b_0$ is a shape factor, with a being related to the active area of the SLM. Since the results of calculations using the RPGBM depend on whether or not noise is included, and the fact that noise is impossible to eliminate experimentally, the remainder of the calculations herein include the effects of noise.

The next consideration entails how changing the number of phase steps, M, influences the parameters in Equation 11. FIG. 3B demonstrates this by comparing the enhancement for different number of phase steps, which is fit to Equation 11. From the fits, it is found that the asymptotic enhancement increases as the number of phase steps increases, while the shape parameter remains constant.

Active SLM Area

In the previous section we calculated the effect of changing bin size on optimization. This represents the first parameter which determines the total number of controllable channels. The other parameter responsible for the total number of bins is the active SLM area, $L^2$, with L being the active SLM side length. For modeling the effect of changing the active SLM area, the following parameters are used: $M=10$ phase steps, a bin size of $b=1$ $\Delta x$, and three different radii $r=\{1 \Delta x', 2 \Delta x',$ and $5 \Delta x'\}$. One then calculates the enhancement as a function of active side length, as shown in FIG. 4A, and finds that it behaves as a Gaussian function as shown by Equation 12:

$$\eta = 1 + \eta_0 \left[1 - \exp\left\{\left(\frac{L}{\beta \Delta L}\right)^2\right\}\right], \quad (12)$$

where $1+\eta_0$ is the asymptotic enhancement and $\beta\Delta L$ is the Gaussian width, with $\beta$ being related to the bin size. Fitting the curves in FIG. 4A one finds that as the integration radius increases both the asymptotic enhancement and the Gaussian width decreases. This implies that to optimize a small radius on the detector requires a much larger portion of the SLM to be active than in order to optimize a large target radius; which is expected given the inverse relationship between distances in the sample and detector planes.

Phase Steps

In addition to being able to change the number of controllable channels on the SLM, the phase resolution of each channel can also be varied. To model the effect of the number of phase steps on optimization the following parameters are used: an integration radius of $r=5\ \Delta x'$, and four total bin numbers $N=\{100, 400, 625, 2500\}$.

Figure 4B:
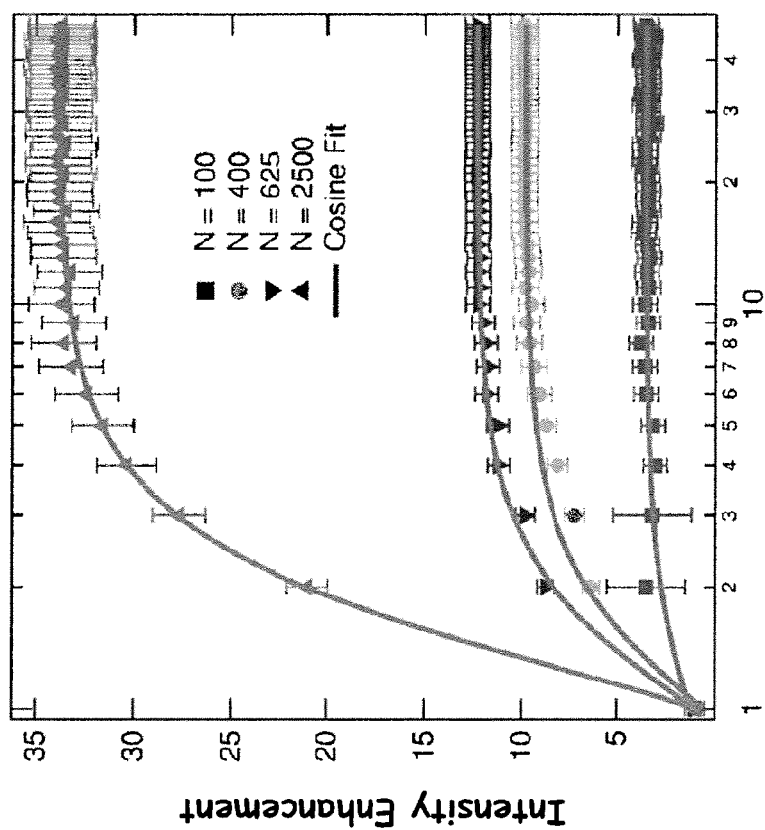
FIG. 4B shows intensity enhancement as a function of the number of phase steps.
Figure 4A:
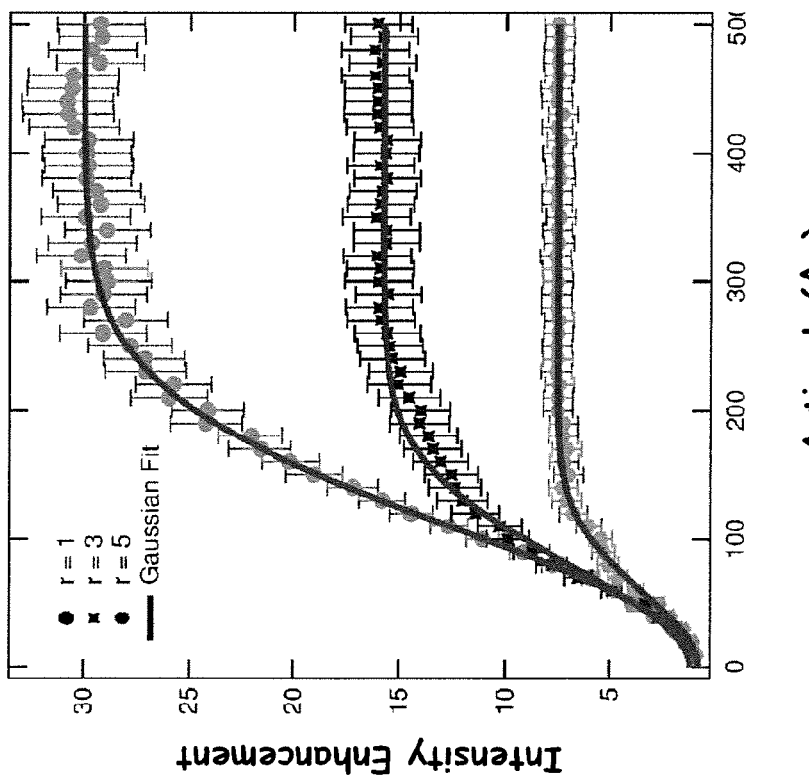
FIG. 4A illustrates modeled intensity enhancement as a function of active SLM side length. The enhancement is found to follow a Gaussian function.

FIG. 4B shows the enhancement as a function of phase steps M, with the enhancement found to quickly saturate at around 10 phase steps for each N value. Qualitatively this dependence can be understood because as the number of phase steps increases the phase resolution increases and at a certain point there will be diminishing returns in trying to attain higher phase resolutions. To understand this behavior, it is to be recognized that the speckle pattern is an interference effect with the optimization process attempting to match the phases of different beam portions to constructively interfere. This implies that the intensity in the target spot depends on a sum of interference terms of the form of Equation 13:

$$A_n \cos(\Phi_n - \psi_n), \tag{13}$$

where $A_n$ is an amplitude factor, $\Phi_n$ is the phase before modulation, and $\phi_n$ is the contribution of the SLM given by Equation 14:

$$\psi_n = \frac{2\pi q_n}{M}, \tag{14}$$

with $q_n$ being an integer corresponding to the phase value giving the largest enhancement. While the exact functionality of the intensity is a complex sum over many such terms, it is found that the enhancement as a function of phase steps follows a function of one interference term given by Equation 15:

$$\eta = 1 + \eta_0 \cos\left(\phi_0 + \frac{\Delta\phi}{M}\right), \tag{15}$$

where $1+\eta_0$ is the asymptotic enhancement and $\phi_0$, $\Delta\phi$ are parameters which determine the shape of the function.

Target Radius

Thus far only the SLM properties have been varied to determine their effects on optimization. However, the detector's parameters can also be controlled; most importantly, the target integration radius can be varied. In order to model the effect of the target radius on enhancement the following parameters are used: $M=10$ phase steps and four different bin sizes such that $N=\{1000, 2000, 5000, 10000\}$. FIG. 5A shows the modeled enhancement which follows a double exponential as a function of the squared integration radius given by Equation 16:

$$\eta = 1 + A_1 e^{-r^2/\sigma_1^2} A_2 e^{-r^2/\sigma_2^2} \tag{16}$$

where $A_1$, $A_2$ are amplitude factors, and $\sigma_1$, $\sigma_2$ are Gaussian widths.

While the decrease in enhancement with increasing target area is expected, the functional form is surprising. To demonstrate this, we derive the expected functional form by recalling that there is a finite amount of power, $P_0$ that can be focused into the integration area. Assuming perfect enhancement in which all the power is focused into the target, one expects, the maximum enhancement for a given radius to be:

$$\eta_{max}(r) = \frac{1}{\langle I_0 \rangle} \frac{P_0}{\pi r^2} \tag{17}$$

where $\langle I_0 \rangle$ is the average intensity before enhancement. However, the RPGBM and experimental results are found to follow Equation 16 and not Equation 17.

Beam Diameter

The last system parameter to consider is the beam diameter. To model the effect of the beam diameter on the enhancement we use the following system parameters: $M=10$ phase steps, four different integration radii, and different bin sizes such that the beam diameter is always 10 bins, (i.e., $b=1$ for a diameter of 10, $b=2$ for a diameter of 20, etc.).

Figure 5B:
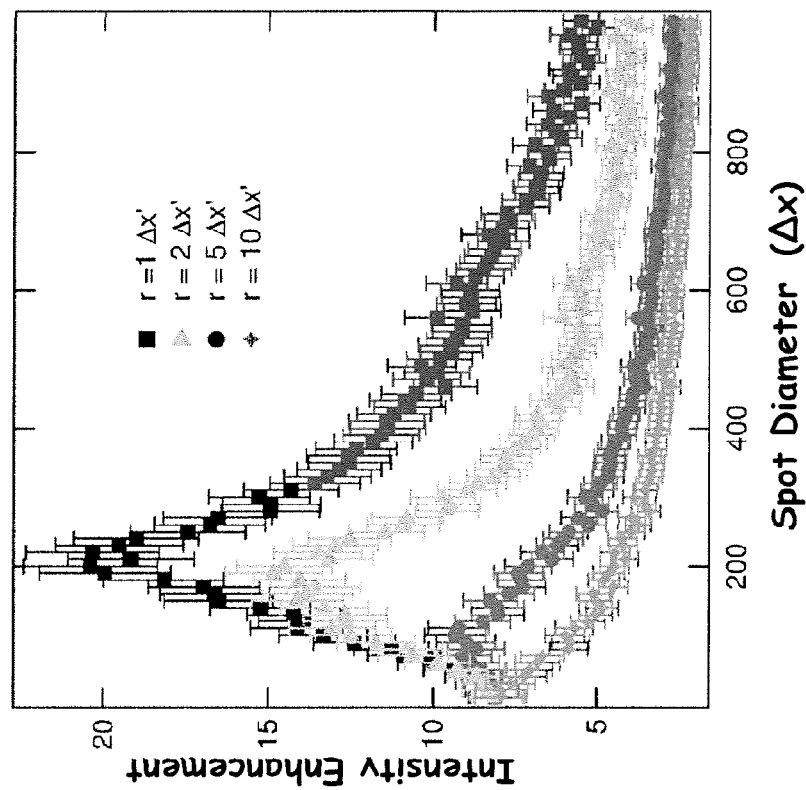
FIG. 5B illustrates modeled intensity enhancement as a function of beam diameter. The enhancement is found to be a peaked function, with the peak location being inversely related to the integration radius used. This result is consistent with the Fourier relationship between the sample and detector planes.
Figure 5A:
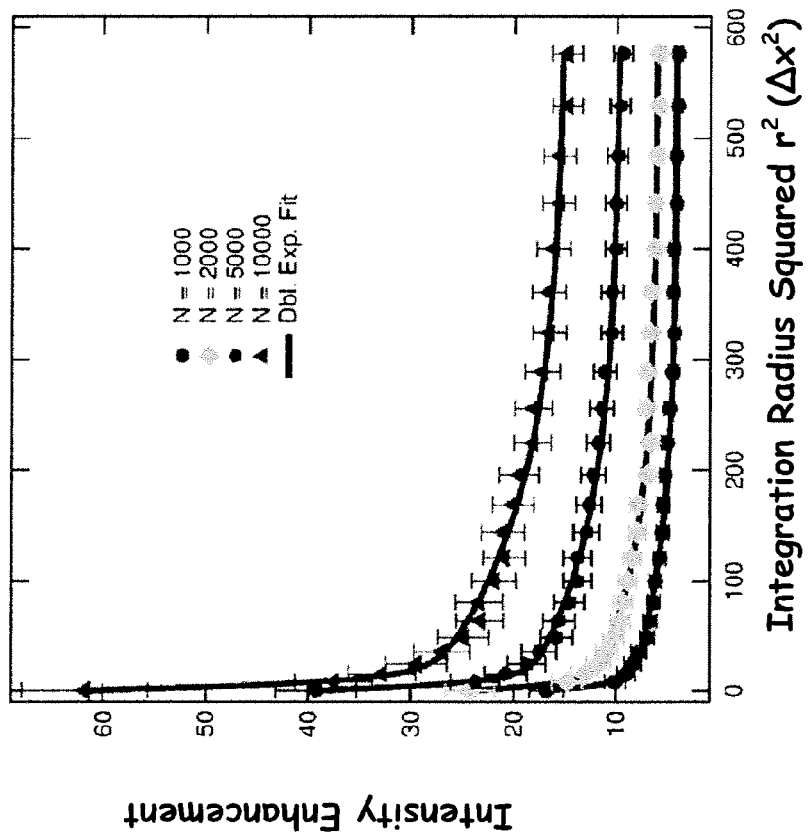
FIG. 5A shows modeled intensity enhancement as a function of squared integration radius for four different bin numbers. The enhancement is found to follow a double exponential decay.

Using these system parameters we calculate the enhancement as a function of beam diameter for different integration radii as shown in FIG. 5B. The enhancement is found to follow a peaked function with the peak location depending on the integration radius used. As the integration radius decreases, the beam diameter corresponding to peak enhancement is found to increase. This suggests an inverse relationship between the beam diameter and target spot size, which is consistent with the Fourier relationship between the sample and detector planes.

Model Summary

We model SLM based transmission optimization using a beam propagation model based on a Gaussian beam with a random phase profile. Using the model and a sequential bin-by-bin optimization algorithm we optimize the intensity in a target area on the detector for different system parameters. From these simulations it is found that the optimization depends on all parameters tested which include: bin size, active SLM area, total number of phase steps, detector integration radius, and on-sample spot size. These results are different than those of previous models, which predict that the enhancement depends on the number of modulated SLM channels (bins) and the signal-to-noise ratio of the system.

In addition to the RPGBM predicting that the enhancement depends on more parameters, it also predicts a different dependence on the number bins used. To derive the enhancements dependence on the number of bins according to the RPGBM we compare Equations 11 and 12. From these equations we find that the scale factors $\alpha$ and $\beta$ relate the two equations with $\alpha=L/\Delta L$ and $\beta=b_0/b$. Substituting the definitions of $\alpha$ and $\beta$ into Equations 11 and 12 we find that the model predicts an intensity enhancement dependence on SLM bin size and active SLM area given by Equation 18:

$$\eta = 1 + \eta_0 \exp\left\{-\left(\frac{Lb_0}{b\Delta L}\right)^2\right\} \tag{18}$$

where $b_0$ is found to be independent of the number of phase steps and $\Delta L$ is found to decrease with increasing integration radius. Recalling that the number of bins is given by $N=(L/b)^2$, one can rewrite Equation 18 in terms of the number of bins:

$$\eta = 1 + \eta_0 \exp\left\{-\frac{N}{N_0}\right\}, \tag{19}$$

Where $N_0=(\Delta L/b_0)^2$. The bin number dependence in Equation 19 is drastically different than predicted by previous models. This difference is due to the RPGBM taking wave propagation effects into consideration, whereas previous models did not.

In addition to predicting the enhancement's dependence on the number of bins, the RPGBM also predicts that the number of SLM phase steps, detector integration radius, and the on-sample beam spot size also affect the intensity enhancement. The dependence on the number of phase steps arises due to optimization being related to controlled interference, while the influence of the integration radius and on-sample beam spot size occurs due to the diffractive nature of the enhancement phenomenon. Since the sample and detector planes are related via a Fourier Transform the effect of changing distances in one plane directly affects distances in the other plane.

Experimental Method, Results and Discussion

To experimentally verify the effects of the various system parameters on transmission optimization we use the apparatus shown in FIG. 1. The controlled transmission system includes a high-speed liquid crystal on silicon spatial light modulator (LCOS-SLM) 18 from Boulder Nonlinear Scientific (BNS), a Coherent Verdi V10 Nd:YVO$_4$ laser source 2, and a high speed Thorlabs CMOS camera detector 3. In order to perform transmission optimization we use an iterative optimization algorithm, similar to that used in simulation.

To keep optimization times manageable, while using an iterative optimization algorithm, the SLM pixels are binned, into N bins with each bin having an edge size of b=L/N, where L is the total number of active pixels on a side. The bins are optimized using M phase steps, of size $\Delta\phi=2\pi/M$. After each update the camera (detector 30) takes an image which is used to calculate the intensity within the target area. After all M steps are completed, the bin's phase is fixed to the phase value corresponding to the largest intensity measured. This procedure repeats for all bins until an optimized phase pattern is displayed on the SLM. Using the iterative optimization algorithm in conjunction with the high speed BNS SLM and high speed Thorlabs CMOS camera results in iteration rates of 160-180 Hz.

To characterize the controlled transmission setup, the five system parameters of note are systematically varied, i.e., bin size, active SLM area, number of phase steps, target area, and beam spot size. Each dependence is measured by varying one parameter, while holding all other parameters fixed, and measuring the change in the intensity enhancement. To obtain better statistics ten optimization runs are performed for each parameter set, from which the average enhancement and error are determined.

In order to separate which effects are due to the systematic parameters and which are due to the opaque sample, five different sample types: ZrO$_2$ particles embedded in polyurethane (PU), ZrO$_2$ particles embedded in polyepoxy (PE), Y$_2$O3 pressed ceramic, ground glass, and printer paper are utilized in performing the measurements. From these measurements it is found that the functional form of the enhancement as a function of system parameters is independent of sample type, with the different samples only affecting fit parameters (e.g., peak enhancement, shape parameters). Thus, the measured dependencies are a function of the optical setup and not the samples. Since the functional forms are consistent across samples; the following sections present the enhancements measured using ground glass as its speckle pattern is found to be the most stable over time and it produces the largest enhancements.

Bin Size

Figures 6A, 6B:
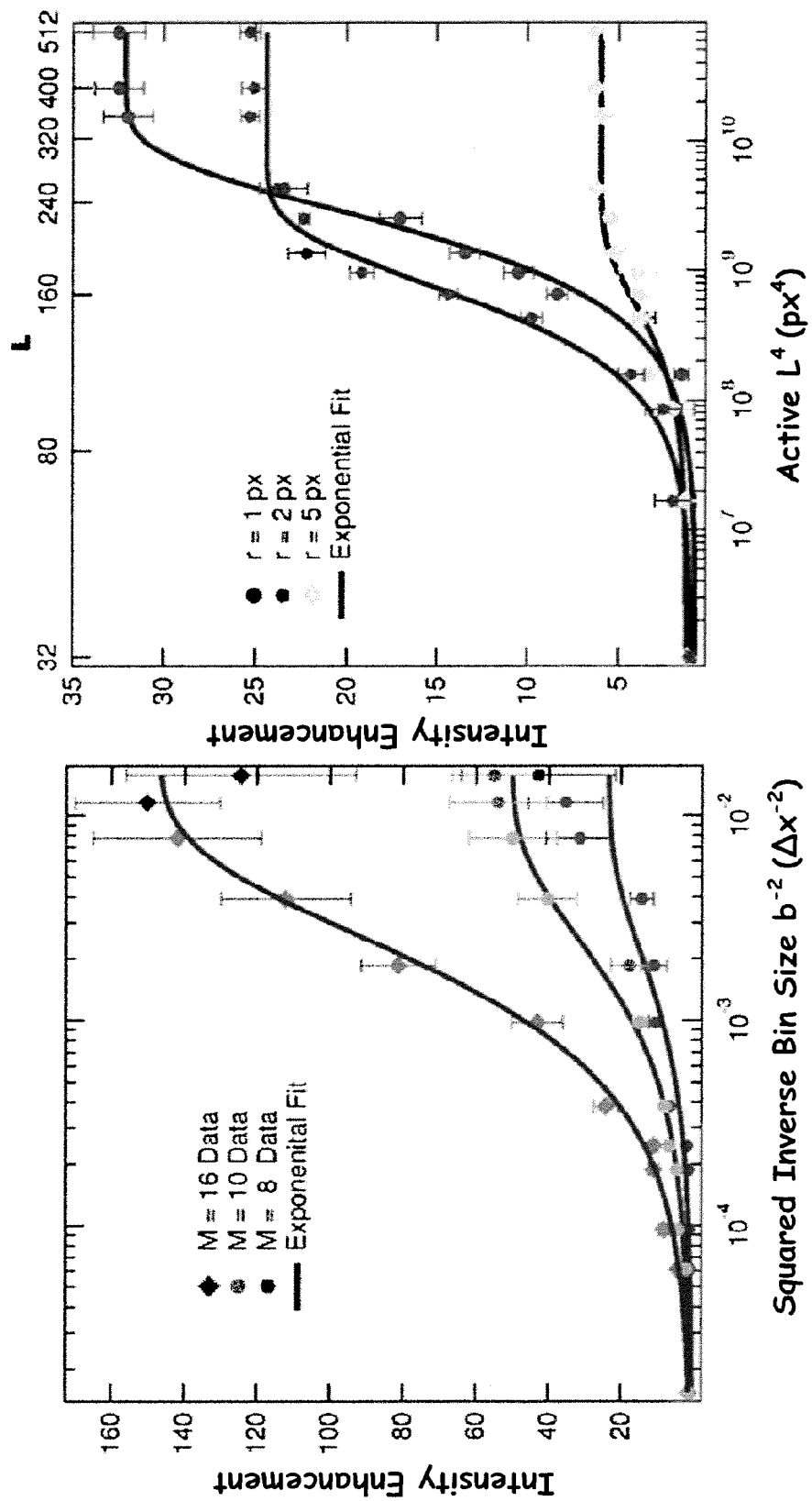
FIG. 6A shows intensity enhancement as a function of squared inverse bin size. The enhancement is found to follow an exponential function, which is consistent with the RPGBM results.
FIG. 6B shows measured intensity enhancement as a function of the quartic active side length, L4. The enhancement is found to follow an exponential function, which is different than predicted by the random phase Gaussian beam model (RPGBM).

The first parameter considered is the bin size. The intensity enhancement is measured at 12 different bin sizes using a beam spot of diameter of about 350 μm, an integration radius of 2 px, and three different total number of phase steps, e.g., M={8, 10, 16}. FIG. 6A shows the enhancement as a function of squared inverse bin size, which is found to follow a function of the form:

$$\eta = 1 + \eta_0(1 - e^{-b_0^2/b^2}), \tag{20}$$

where $1+\eta_0$ is the asymptotic enhancement and $b_0$ determines the enhancement's shape. The parameters $\eta_0$ and $b_0$ are determined for each M value by fitting the curves in FIG. 6A, and are tabulated in Table II.

TABLE II

Fit parameters from Equation 20 for the intensity enhancement as a function of bin size.

| M | $\eta_0$ | $b_0$ |
|---|---|---|
| 8 | 23.4 ± 4.9 | 21.4 ± 3.5 |
| 10 | 50.1 ± 7.2 | 19.9 ± 1.9 |
| 16 | 146 ± 14 | 19.5 ± 1.3 |

From Table II we find that the asymptotic enhancement increases with the number of phase steps, while the shape factor, $b_0$, is found to be constant within uncertainty. These results are functionally consistent with the RPGBM results. The difference in the magnitude of enhancement between model and experiment is due to three factors: 1) imperfect matching of parameters between experiment and modeling, 2) different noise levels, and 3) a divergence between the model and experiment related to the number of phase steps, as discussed below.

SLM Cropping

The next parameter tested is the active SLM area with optimization performed using a spot diameter of about 200 μm, a bin size of b=8 px, M=8 phase steps, and three different integration radii, r={1 px, 2 px, 5 px}. The enhancement is measured first with the full SLM active, after which the outer rows/columns are "shut off" such that the active area is always a centered square and optimization is performed again. This is continued until only a 4 bin×4 bin (32 px×32 px) area remains active. FIG. 6B shows the intensity enhancement as a function of quartic active side length, $L^4$. From FIG. 6B, we find that the enhancement, as a function of active length, L, behaves functionally as:

$$\eta = 1 + \eta_0\left[1 - \exp\left\{\left(\frac{L}{\Delta L}\right)^4\right\}\right], \tag{21}$$

where $\Delta L$ is a width parameter and $1+\eta_0$ is the asymptotic enhancement. From Equation 21 we find that the explicit dependence of the enhancement on active side length is different than predicted by RPGBM (i.e., Gaussian in L for the RPGBM and Gaussian in $L^2$ for experiment).

A possible explanation for this discrepancy is related to how the RPGBM treats SLM cropping versus the real world implementation. In the RPGBM, cropping of the active SLM area is implemented by shutting off modulation in grid points that represent the sample's exit plane. However, in reality, SLM cropping shuts off modulation of portions of the light incident on the sample. The modulated light incident on the sample is then transmitted through the sample with various spatial components interfering. This interference is not accounted for in the RPGBM, which could lead to the divergence between the RPGBM and experiment.

Despite the explicit dependence on L being different, the general dependence—enhancement increasing to a constant value as L increases—is consistent. Additionally, we find that the behavior of the enhancement's fit parameters behave as expected for changing target radii. To demonstrate this consistency, we fit FIG. 6B to Equation 21 and find $\eta_0$ and $\Delta L$ for each integration radius tested. Table III, shown below, compiles the fitting results. Both the amplitude, $\eta_0$, and width parameter, $\Delta L$, are found to decrease with increasing integration radius, which is predicted by the RPGBM.

TABLE III

Fit parameters from Equation 20 for the intensity enhancement as a function of active area. Both $\eta_0$ and $\Delta L$ decrease with increasing integration radius, which is consistent with the RPGBM.

| r | $\eta_0$ | $\Delta L$ |
|---|---|---|
| 1 | 32.10 ± 0.80 | 232.6 ± 3.6 |
| 2 | 24.36 ± 0.25 | 168.3 ± 1.9 |
| 5 | 5.94 ± 0.11 | 156.4 ± 3.6 |

Phase Steps

Lastly, we vary the number of phase steps used during optimization. For these measurements, we use a spot diameter of about 350 μm, an integration radius of 2 px, and three bin sizes: b=16 px, b=32 px, and b=64 px. The enhancement is found to depend on the number of phase steps, M, as:

$$\eta = 1 + \eta_0 \cos^p\left(\frac{\pi}{2M}\right), \quad (22)$$

where $1+\eta_0$ is the asymptotic enhancement and p is an exponent which controls the shape of the function. While the RPGBM predicts that p=1, we find from fitting experimental results that p>1 and decreases as N increases, as shown in Table IV below. This result is unexpected and the underlying mechanism is currently unknown.

TABLE IV

Fit parameters from Equation 22 for the intensity enhancement as a function of the number of phase steps.

| N | $\eta_0$ | p |
|---|---|---|
| 64 | 65.5 ± 6.4 | 61.0 ± 5.3 |
| 256 | 78.8 ± 6.4 | 59.2 ± 6.5 |
| 625 | 95.3 ± 4.1 | 53.5 ± 8.6 |
| 1024 | 116.0 ± 8.2 | 29.0 ± 3.5 |

One possible explanation is that realistic samples complicate the coupling between the modulated phase incident on the sample and the phase exiting the sample such that only a fraction of the light exiting the sample has an optimized phase. The result of having less control would be to decrease the enhancement, which is consistent with p>1.

Also, in this case it would be expected that the effects due to the sample will decrease as N increases, since the size of the modulated area decreases and gives a greater control over transmission through the sample. This increased control would cause p to decrease, which is observed experimentally.

Target Radius/Area

Figures 7A, 7B:
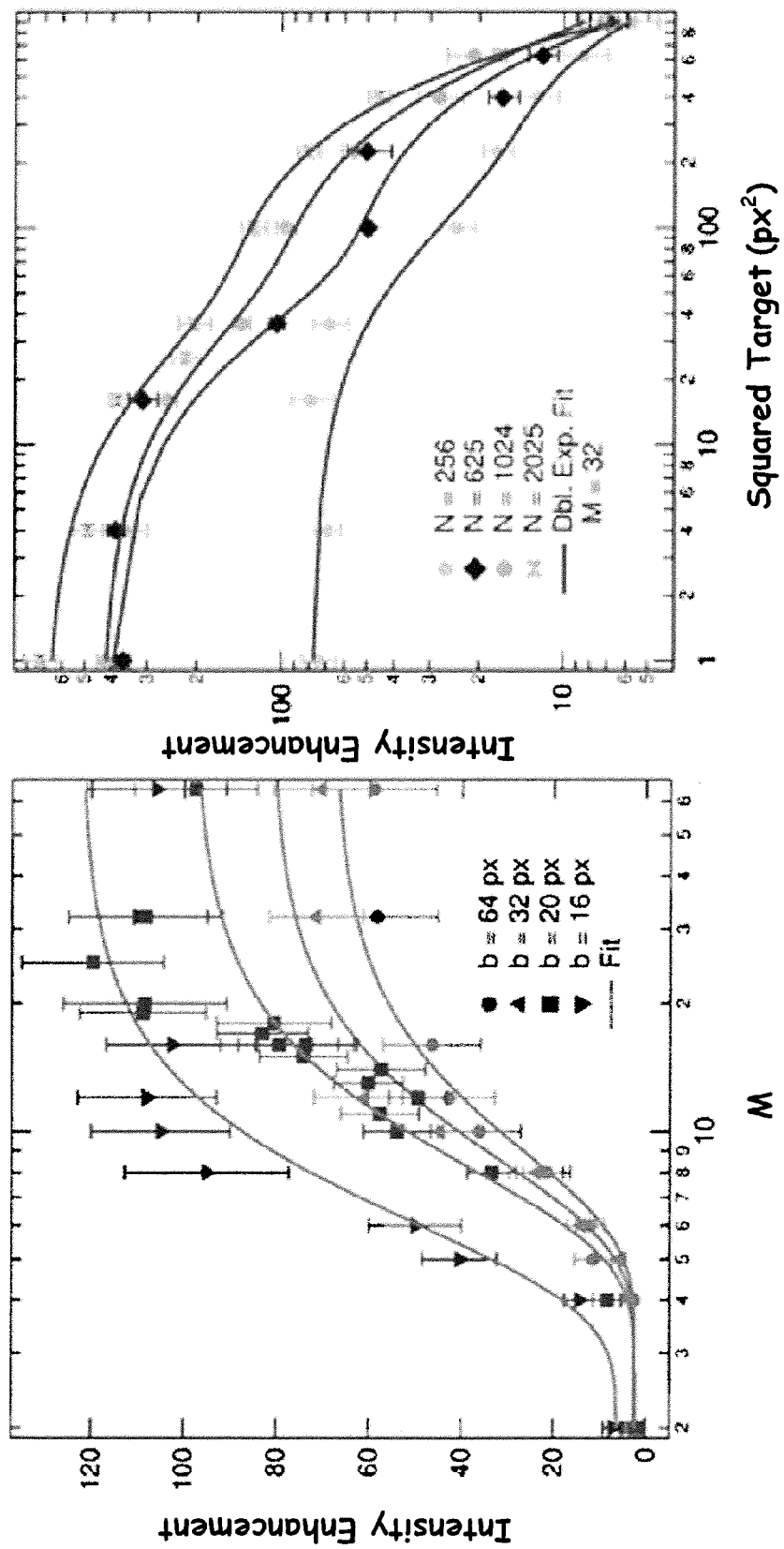
FIG. 7A illustrates intensity enhancement as a function of phase steps.
FIG. 7B shows intensity enhancement as a function of integration radius measured using ground glass with 32 phase steps, a spot size of 380 µm and four different total number of bins. The enhancement is found to behave as a double exponential which is consistent with the random phase Gaussian beam model (RPGBM).

Thus far only the effects of SLM parameters have been considered. At this point we consider the enhancement's dependence on target radius. We measure the intensity enhancement using a beam spot size of 380 μm, M=32 phase steps, four different numbers of bins, N={256, 625, 1024, 2025}, and nine integration radii/areas. The measured enhancement as a function of integration radius, shown in FIG. 7B, is found to behave as the sum of two Gaussians. This behavior is identical to the RPGBM.

We fit the enhancement as a function of integration radius to Equation 16 and find the different Gaussian fit parameters as a function of bin number. Table V compiles the fit results, as shown below.

TABLE V

Fit parameters from Equation 16 for the intensity enhancement as a function of integration radius.

| N | A1 | σ1 | A2 | σ2 |
|---|---|---|---|---|
| 256 | 22 ± 13 | 27.1 ± 5.5 | 56 ± 12 | 7.4 ± 1.5 |
| 625 | 67.1 ± 3.3 | 19.1 ± 1.7 | 344 ± 17 | 4.23 ± 0.18 |
| 1024 | 129 ± 16 | 15.85 ± 1.66 | 312 ± 33 | 3.95 ± 0.38 |
| 2025 | 190 ± 19 | 16.10 ± 0.91 | 496 ± 71 | 3.77 ± 0.35 |

The amplitudes are found to increase with bin number—consistent with the RPGBM—and the widths are found to decrease as the bin number increases. Additionally, the Gaussian widths appear to reach a constant value as the number of bins increases, with the widths for N=1024 being within uncertainty of those for N=2025.

As with the RPGBM model's results, the underlying mechanism behind the experimental enhancement's target area dependence is currently unknown. Given that both the model and experiment have the same functional dependence it can be deduced that the physical phenomenon responsible is related to beam propagation effects.

Spot Size

Figures 8A, 8B:
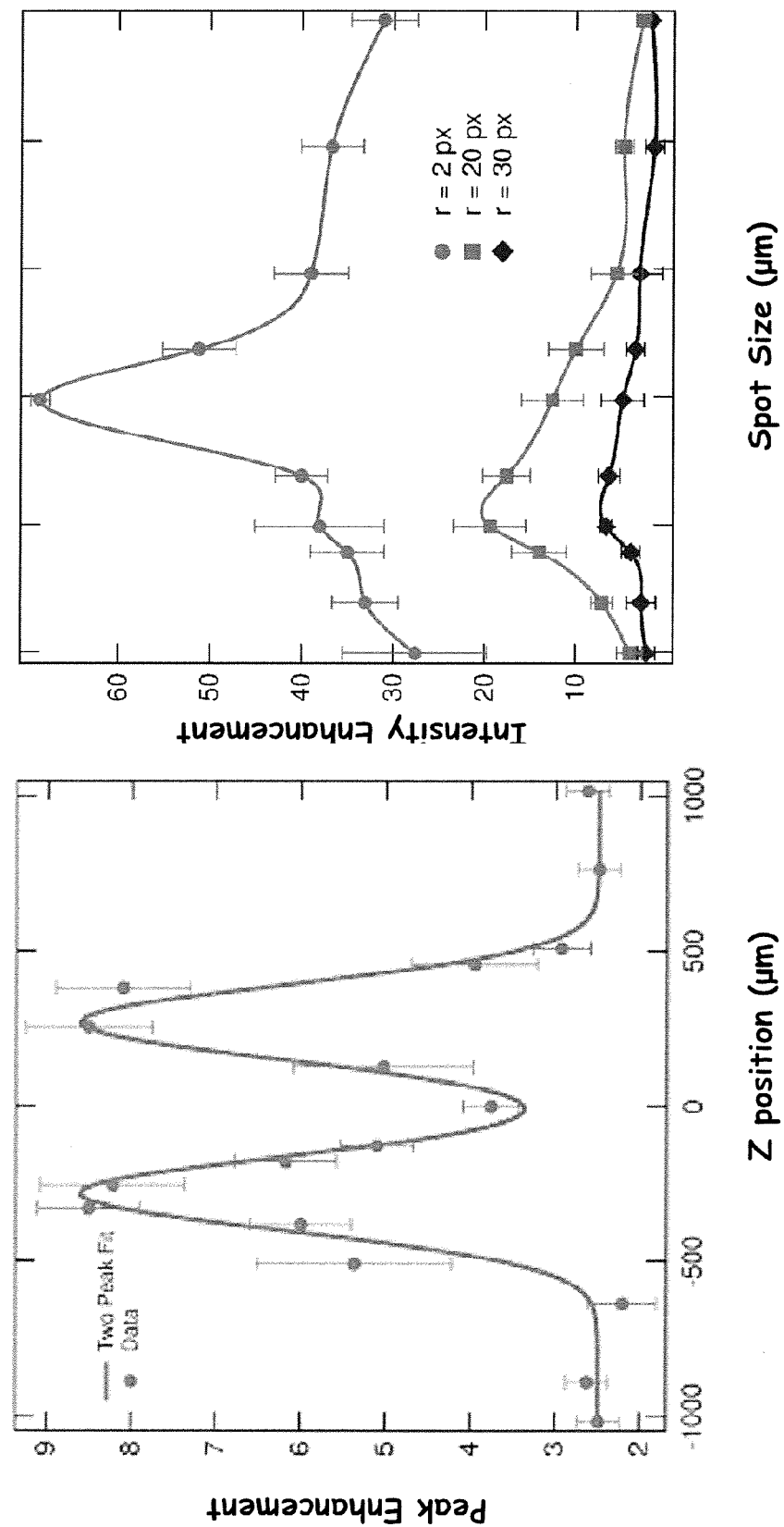
FIG. 8A shows peak enhancement as a function of position along the optical axis, where z=0 is the focal point of the focusing lens. The spot size at z=0 is about 0.9 µm.
FIG. 8B shows measured intensity enhancement as a function of the on-sample spot size. The enhancement is found to follow a peaked function with the peak location being inversely dependent on the integration radius, consistent with the random phase Gaussian beam model (RPGBM) result.

The last system parameter varied is the on sample beam spot size. To measure the enhancement's spot size dependence we use N=1024 bins, M=16 phase steps, and integration radii of 2 px, 20 px, 30 px. The enhancement is first measured with the sample positioned within the focal length of the focusing objective 26, as shown in FIG. 1A, such that the on-sample beam diameter is 600 μm. After the initial measurement, the sample is systematically translated and the enhancement is measured at fixed z positions until the sample translates through the focal point and reaches an on-sample beam diameter of 600 μm again. FIG. 8A shows the peak enhancement as a function of position along the optical axis, where z=0 is the focal point of the focusing lens.

From FIG. 8A we find that the enhancement is symmetric about the focal point, with the peak value occurring at a nonzero distance from the focal point. The z-position can be converted into the spot diameter, 2w, using ray matrix Gaussian beam propagation. Assuming that the beam incident on the focusing lens is near the beam waist, the Gaussian width, w, at position z is given by:

$$w(z) = \frac{1}{kfw_0}\sqrt{4f^2(f+z)^2 + k^2w_0^4 z^2} \qquad (23)$$

where $w_0$ is the beam diameter at the focusing lens, f is the focal length of the lens, and $k=2\pi/\lambda$ where $\lambda$ is the wavelength of light. Note that Equation 23 is symmetric about the focusing lens's focal point. Therefore we average the enhancement measured on both sides of the focal point to find the intensity enhancement as a function of spot diameter, which is shown in FIG. 8B.

The experimentally measured intensity enhancement is found to peak at a nonzero spot diameter, with the diameter corresponding to peak enhancement increasing as the integration radius decreases. Additionally the width of the peaked function is found to decrease as the integration radius decreases. These behaviors are consistent with the prediction of the RPGBM.

Different Samples

The experimental enhancement's dependence on the different systematic parameters diverges from previous prior art models and the RPGBM. While the RPGBM predicts similar behavior to experiment, some of the dependencies are functionally different. The most likely source of divergence between experiment and the RPGBM is the model's treatment of the sample as a "black box". This treatment predicts that the enhancement is independent of the sample properties (e.g. sample thickness and scattering length).

While a precise characterization of the enhancement's dependence on sample parameters is not discussed herein, a simple direct comparison between six non-limiting example samples is considered: paper, ground glass, $Y_2O_3$ ceramic, and three formulations of $ZrO_2$ particles embedded in polymers. Optimization is performed using the same experimental parameters (b=16 px, M=32, r=2 px, w=250 μm) at five different points on each sample to find the spatially averaged intensity enhancement, which is tabulated in Table VI below. From Table VI one can see a wide variation in enhancement when using different samples, with the largest enhancement being 36×larger than the smallest.

TABLE VI

Maximum enhancement obtained for different samples using system parameters of b = 16 px, M = 32, r = 2 px, w = 250 μm. There is a 36× difference between the smallest and largest enhancement.

| Sample | Thickness (μm) | Scattering Length (μm) | Enhancement |
|---|---|---|---|
| Ground Glass | 1564 ± 75 | 970.7 ± 2.1 | 172 ± 12 |
| Paper | 85.1 ± 6.4 | $(2.654 \pm 0.026) \times 10^{-3}$ | 9.4 ± 1.0 |
| 10 wt % $ZrO_2$ NP/PU | 867 ± 67 | 4.11 ± 0.28 | 5.50 ± 0.45 |
| 10 wt % $ZrO_2$ NP/PE | 1036 ± 50 | 3.9 ± 1.2 | 4.79 ± 0.49 |
| 1 wt % $ZrO_2$ NP/PU | 959 ± 37 | 50.8 ± 3.1 | 44.45 ± 1.2 |
| $Y_2O_3$ Ceramic | 358 ± 44 | $(2.944 \pm 0.029) \times 10^{-2}$ | 12.8 ± 1.3 |

Several possible factors from these example measurements which may affect the enhancement can be deduced: the sample persistence time and scattering length. The first factor, the persistence time, is a measure of how long a sample produces the same speckle pattern; which directly affects how well an SLM system can optimize transmission. From the measurements provided herein, one finds that the ground glass and particle (NP) samples have stable speckle patterns over a period of days, while the paper's speckle pattern changes in tens of minutes. This results in paper having a relatively low enhancement despite being the thinnest sample. While the persistence time is important to optimization it is to be appreciated that the enhancement is largest for large scattering lengths (e.g., ground glass) and smaller for small scattering lengths (e.g., particles embedded in polymers).

Other Beneficial System Configurations

Once the SLM has been optimized for the specific measurement, its phase settings, as discussed above, can be used as a key that represents the optical properties of the extrinsic surface marker and/or intrinsic surface. Attempts to replicate the extrinsic surface marker and/or intrinsic surface features invariably leads to a different key. Similarly, tampering with the extrinsic surface marker and/or intrinsic surface features leads to changes in the surfaces scattering properties leading to a different key.

In addition to the transmission geometry of system 100 shown in FIG. 1A, it is also beneficial to use a reflection geometry, as also shown in FIG. 1B, as now shown in FIG. 9A and FIG. 9B, with FIG. 9A an exemplary schematic of a system based on a transmissive SLM 18 (labeled 200A) and FIG. 9B an exemplary schematic of a system based on a reflective SLM (labeled 200B). Note that FIG. 9A and FIG. 9B are general schematics and that in practice can include additional optics, electronics, algorithms, and other surface types.

System 200A includes an optical source of radiation (e.g. as described above) 2, an SLM 18, focusing lens or lens system 26, extrinsic surface marker or intrinsic surface feature 28, and a detector 30 either positioned in an off axis configuration (see inset FIG. 9A') or on axis configuration, as shown in FIG. 9A, with the addition of a beamsplitter 16 and/or dichroic mirror. System 200B is similar to 200A with an optical source of radiation 2, a reflective SLM 18', focusing lens or lens system 26, extrinsic surface marker or intrinsic surface feature 28, and a detector 30 either positioned in an off axis configuration (see inset FIG. 9B') or on axis configuration (with the addition of a beamsplitter 16 and/or dichroic mirror, as shown in FIG. 9B), but it is noted that system 200B uses the beamsplitter 16 and/or mirror in order to use a reflective SLM 18' geometry.

In this configuration, an extrinsic surface marker, placed on an item 29 to secure, or intrinsic surface features of the item to secure are used as the PUF. The SLM modulates the wavefront from the optical source, which is focused onto the PUF. The optical response of the PUF (e.g. speckle pattern, fluorescence spectrum, RL spectrum, etc.) is then measured using either an appropriate on-axis or off-axis detector, which operates in a closed feedback loop with the SLM to optimize the optical response to conform to a desired response (e.g. focal spot, intensity pattern, spectrum, etc.). The optimal wavefront and optimal optical response so determined are then stored in memory, such that at a later time the surface can be reinterrogated with the optimal wavefront and the surface's optical response can be measured and compared to the optical response stored in memory. If the surface's optical response is found to have changed, such that the comparison fails, it is an indicator that the secured item has been tampered with, either intentionally or unintentionally.

Figure 10A:
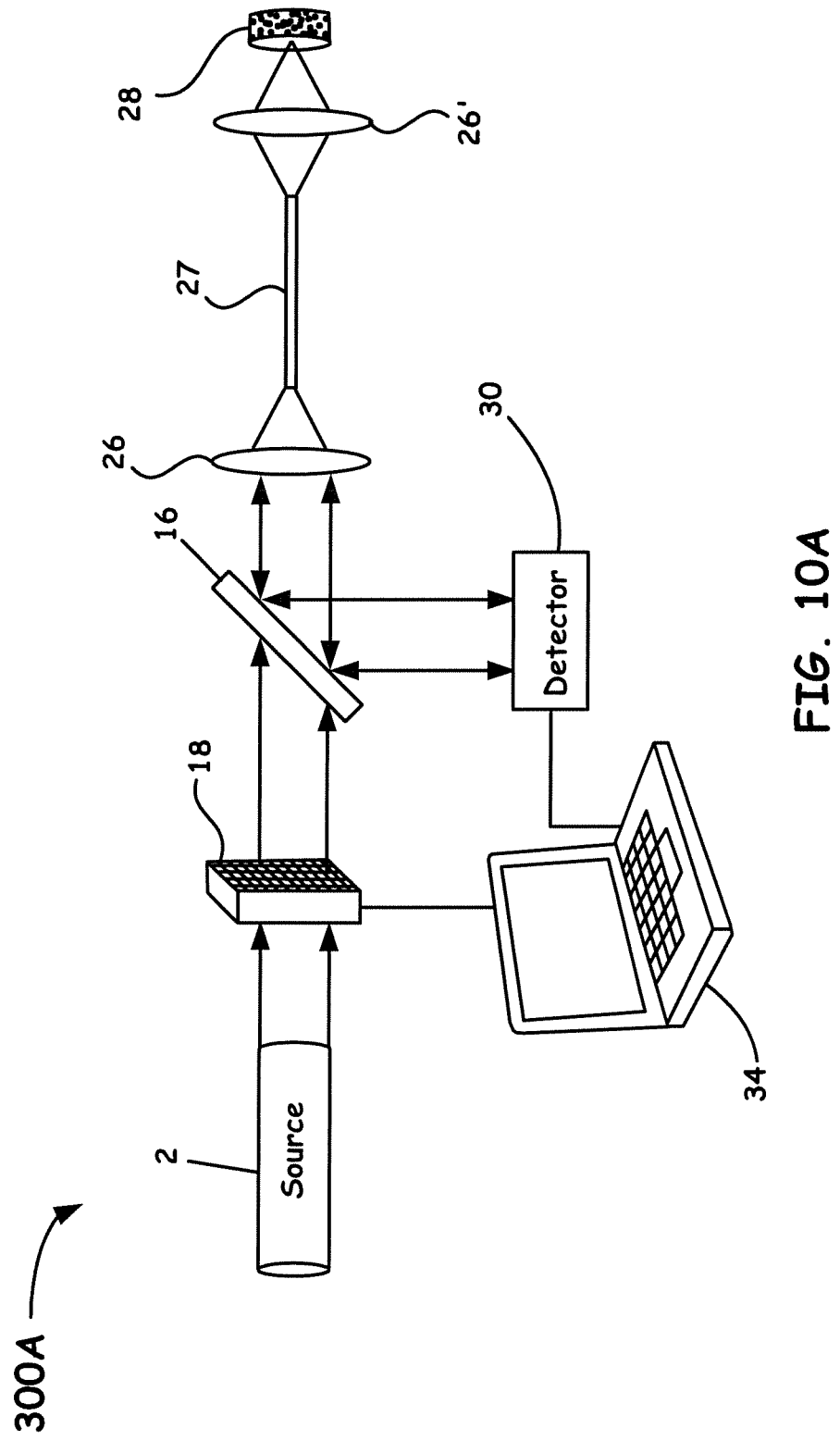
FIG. 10A shows a general example embodiment of remote "off-site" spatial-light-modulator-based authenticating system to characterize signatures of scattering composites and/or original object features.

While systems 100A, 100B, 200A, and 200B are shown in close proximity of the surface being interrogated, the basic concept can also be applied in an "off-site" configuration, in which the authenticating system is connected to the surface to be interrogated via a multimode optical fiber (MMOF). FIG. 10A shows a schematic of such a system with the reference numeral 300A. Note that FIG. 10A and FIG. 10B, and FIG. 1A share numeration for similar components.

The basic components of system 300A shown in FIG. 10A are an optical source of radiation (e.g. as described above) 2, an SLM 18, beamsplitter/dichroic mirror 16, focusing lens or lens system 26, 26', a multimode optical fiber (MMOF) 27, an extrinsic surface marker or intrinsic surface feature 28, and a detector 30. In this configuration the source wavefront is passed through a transmissive SLM 18 (or reflected from a reflective SLM 18' with appropriate optics) and focused onto the MMOF 27. The wavefront transmitted through the MMOF 27 is then focused onto the surface (e.g., 28) to be interrogated, using appropriate optics, and the optical response (i.e. speckle pattern, fluorescence spectrum, random lasing spectrum, etc.) is coupled back into the MMOF 27, with the beamsplitter 16/dichroic mirror separating the optical response out to be measured by the detector 30. The optimization and verification procedure is then the same as above, with the primary difference being the use of the MMOF 27 to allow for "off site" verification.

Figure 10B:
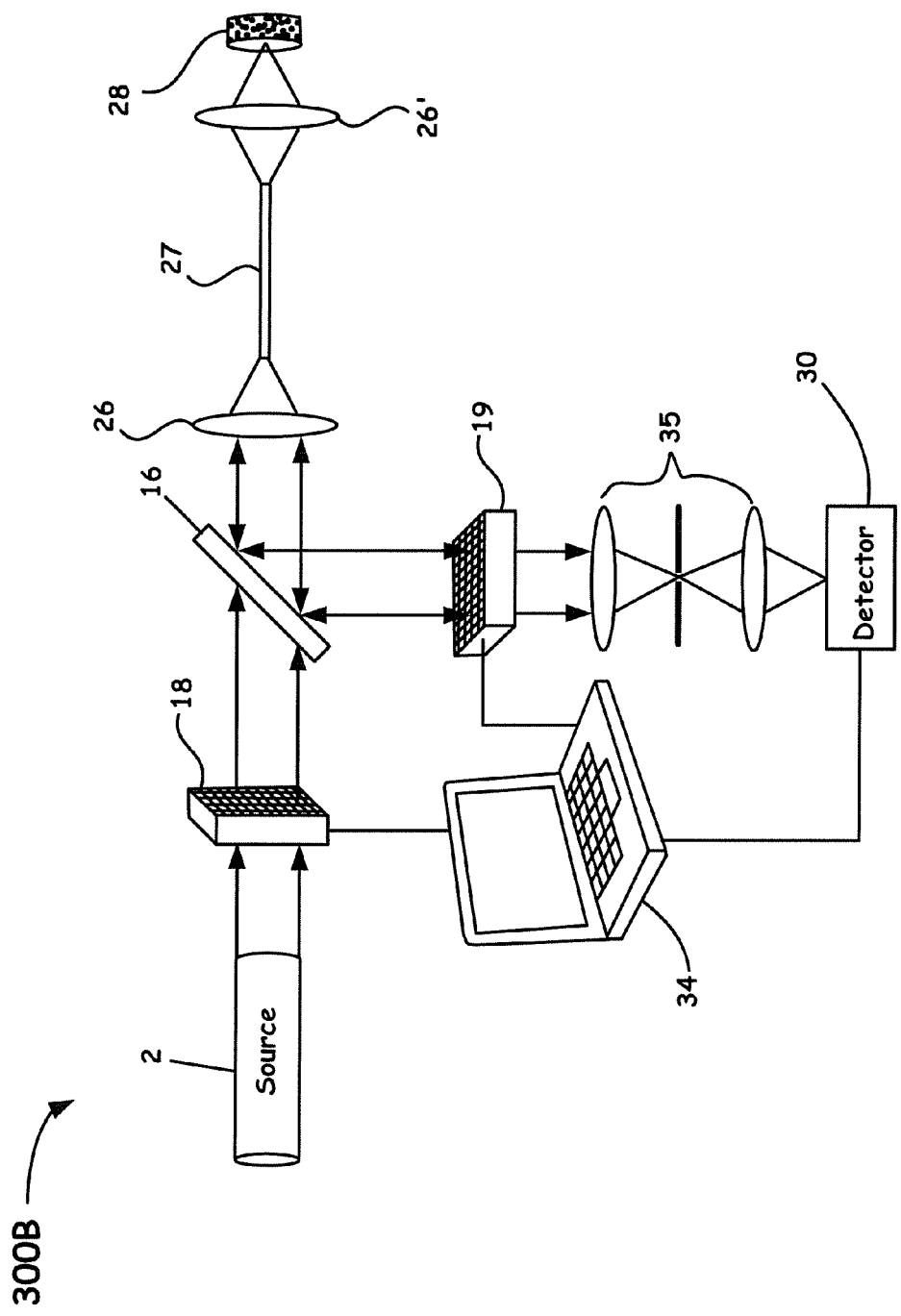
FIG. 10B shows a general example of a quantum secure authentication embodiment of remote "off-site" spatial-light-modulator-based authenticating system to characterize signatures of scattering composites and/or original object features.

In addition to the basic setup shown in FIG. 10A, system 300A can be further secured by use of Quantum Secure Authentication (QSA). FIG. 10B thus shows a schematic of system 300A with the additional components required for QSA, generally labeled 300B. System 300B includes the components of system 300A, as discussed above, as well as a second transmissive SLM 19 (or a reflective SLM 18' with appropriate optics), and a spatial filter (lens and pinhole) 35.

QSA takes advantage of the unclonable nature of quantum states in order to disguise the challenge (wavefront), thereby preventing an adversary from manipulating the response. Different approaches to producing these quantum states include, but are not limited to: coherent states with low mean photon numbers, single or bi-photon states, squeezed states, etc. In the configuration of system 300B we use coherent states with low mean photon numbers.

For the implementation of QSA in system 300B we use the light source and first SLM to highly complex wavefronts with low numbers of coherent photons. The optical response from the sample is then measured using a phase-sensitive detector, from which the phase conjugate of the response can be determined and stored. The stored phase conjugate is then used with the second (analyzer) SLM to modulate the surface's optical response. If the surface's optical response, at a later time, is unchanged, the phase conjugate modulation will cause the wavefront to focus through the spatial filter resulting in a focal point on the detector. If the response has changed, phase conjugate will result in the wavefront scattering from the spatial filter producing a speckle pattern.

The purpose of the quantum-secure authentication (QSA) method disclosed herein and as shown by the example embodiment in FIG. 10B is to prevent adversaries from interfering with the authentication process. If an adversary is familiar with the authentication process and the behavior of the key in response to a challenge, he/she can possibly intercept the optical signals (in cases of remote authentication using a fiber-optical cable), measure the challenge, and then use a spatial light modulator similar to those shown in FIG. 10A and FIG. 10B to generate an appropriate response.

For example, if the challenge/response relied on calculating the phase conjugate in order to achieve a focal spot on the detector, the adversary might use a phase sensitive detector to measure the challenge and then calculate and launch the phase conjugate, resulting in a focal spot on the detector even though the challenge never interacted with the key.

QSA thus beneficially capitalizes on unclonable properties of quantum states to hide the challenge, thereby preventing the adversary from emulating the response. Other approaches to be utilized herein include coherent states with low mean photon numbers, single or bi-photon states, squeezed states, etc. The approach most often used herein is based upon coherent states with low mean photon numbers and is implemented by using light pulses with low photon numbers but wavefronts of high complexity for the challenge. Thus first SLM 18 can be configured to generate a different challenge for each pulse. A large number of challenges is then sent to the key and the response measured using a photon-counting detector. Because of the small photon number and the large number of challenges, an adversary is only able to obtain a small amount of information and thus the true PUF 28 can easily be separated from random and optimal attacks.

Another beneficial technique that can be utilized in conjunction with the systems disclosed herein is the Gabor transform. The Gabor transform takes two-dimensional speckle images and converts them into a one-dimensional key (bit-string). Using SLM wavefront shaping with one of the systems described above, the speckle pattern from an intrinsic surface or extrinsic surface marker can be measured and converted into a one-dimensional key using the Gabor transform, which then can be stored. At a later point the surface can then be interrogated with the "challenge" wavefront and the surface's responding bit-string can be compared to the stored value to determine authenticity. This authentication scheme has the added benefit of using error correcting codes to account for the effects of systematic noise.

Alternatively, the 2D speckle pattern can be used to calculate a specific challenge that results in an easily recognizable response. For example, the phase conjugate of the speckle pattern can be calculated, as generated via an SLM (e.g., 18), and then used as the challenge. Depending on the specific optics used during the measurements, the response can either be a flat intensity distribution across the detector 30 (e.g., a CCD camera) or a focal spot in the center of the detector 30 (e.g., a CCD camera). In the latter case, the detector 30 (e.g., a CCD camera) can be replaced by a simple detector and the intensity level can be measured, simplifying the response process. This arrangement is particularly suitable for integration of a quantum-secure authentication processes, as discussed above for system 300B, as shown in FIG. 10B.

Tamper Indication Tests of Surface Marker O-PUFs

This section presents example results reporting on the tamper-indicating ability of O-PUFs used in connection with authentication system configurations disclosed herein. Tamper testing of O-PUFs was performed using brute force mechanical, thermal, and chemical attacks. Tests also evaluated O-PUF "unclonability".

Methods

A nanocomposite consisting of transparent polymer dispersed nanoparticles (NP) was used as a sample O-PUF surface marker. Polymers are chosen as the host material as their properties can be widely tuned based on composition and can be easily applied to a variety of surfaces. To simplify implementation and production ten different commercially available polymers were chosen as possible hosts. These polymers include: polyurethanes (PUs), polyepoxies, and cyanoacrylates. While these polymers may be viable hosts for the nanocomposites, there are several real world factors which are important to consider in selecting an exemplary polymer. Namely, in order to be viable O-PUFs, the polymer must possess temporal stability (i.e., can't deform over time), environmental stability (including temperature, humidity, UV and ionizing radiation), and a reasonable cure time.

Based on these practical requirements initial testing was performed for each sample polymer to determine its environmental stability and cure time. Rigid and flexible PUs were found to be the most stable polymers of those tested.

Figure 11B:
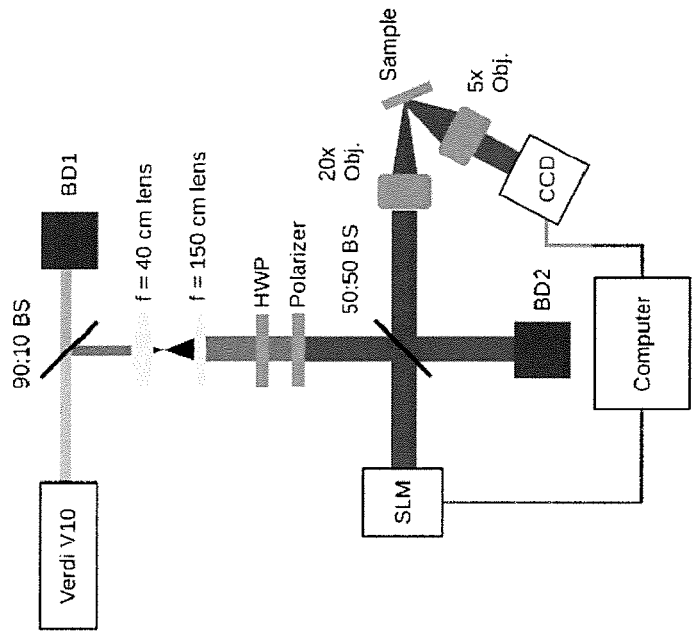
FIG. 11B is a schematic of an example reflective based authentication system in an off-axis configuration.
Figure 11A:
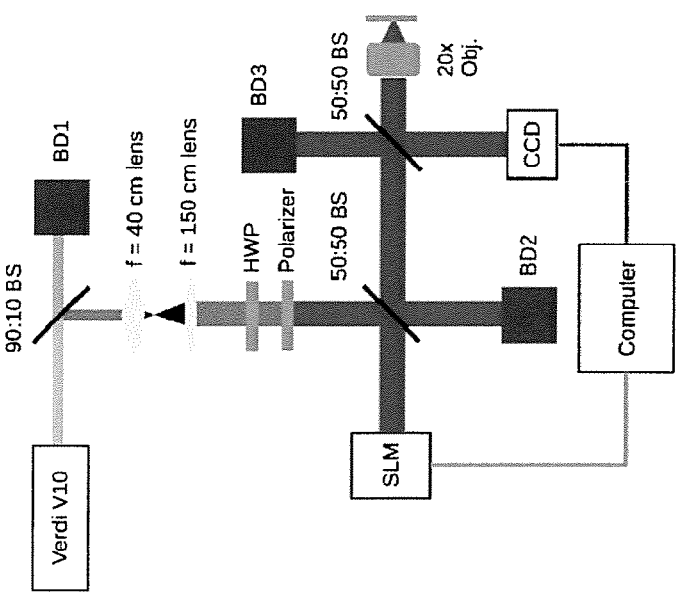
FIG. 11A is a schematic of an example reflective based authentication system in an on-axis configuration.

The reflective based optical system used was consistent with FIG. 1 herein. The system consisted of a Coherent Verdi V10 Nd:YVO$_4$ diode-pumped solid state laser; a Boulder Nonlinear Systems (now Meadowlark) liquid crystal on silicon SLM (LCOS-SLM); a Thorlabs DCC1545M CMOS camera; and beam conditioning and focusing optics, including polarizers, lenses, beamsplitters, and Mitoyo high working distance objectives. The Verdi was operated at 10 W where its operation is most stable. As this power is above the SLMs damage threshold the laser was passed through a 90:10 beam splitter with 9 W dumped into a beam dump and the other 1 W passed through a 4.5× beam expander and a halfwaveplate (HWP)/polarizer pair to provide intensity control. The expanded beam was then split by a 50:50 beam splitter, with half of the light directed onto the SLM and the other half directed into a beam dump. Once modulated by the SLM the light was reflected back through the beam splitter and passed to the sample, with the sample side optics dependent on the detectors location. If the reflective-based optical system is used in the off-axis detector configuration, the modulated light is directly focused using a 20×HWD objective onto the surface marker. The backscattered light was then collected by an off-axis 5×HWD objective and projected onto the detector. FIG. 11B shows a schematic of this geometry. On the other hand, if the reflective-based optical system is operated in an on-axis detector geometry, the modulated light is passed through another 50:50 beam splitter and is focused onto the sample using a 20×HWD objective. The back scattered light is then collected by the same objective and projected back to the beam splitter, where it is reflected into the detector. FIG. 11A shows the schematic for this geometry. The light scattered from the surface marker and collected onto the CMOS detector produces, in general, a speckle pattern which depends on the settings of the system, in particular the settings of the SLM. By systematically varying the system parameters (e.g., the SLM parameters) the laser's wavefront is shaped such that the reflected speckle pattern is transformed into a single focal point on the detector. This procedure is accomplished by a feedback loop between the detector and SLM, with the feedback loop controlled by an optimization algorithm, as discussed above. For the purposes of this example test three different optimization algorithms were used: an iterative algorithm (IA), a simple genetic algorithm (SGA), and a micro-genetic algorithm (µGA).

Once optimization is complete the resulting SLM settings and detector image become the O-PUFs unique optical signature. Any change to the sample or SLM settings will lead to the backscattered light no longer being optimally scattered, resulting in the detector seeing a speckle pattern instead of a focal point. In order to quantify the similarity between the ideal detector pattern and a pattern measured at a later time Pearson's correlation coefficient was used. Pearson's correlation coefficient is defined as $$c \equiv \frac{\sum_{i,j}^{N}(I_{i,j} - \bar{I})(I_{0;i,j} - \bar{I_0})}{\sqrt{\sum_{i,j}^{N}(I_{i,j} - \bar{I})^2 \sum_{i,j}^{N}(I_{0;i,j} - \bar{I_0})^2}}, \quad (24)$$

where $I_{0;i,j}$ is the initial optimized detector pattern, $I_{i,j}$ is the new pattern, with the subscripts i and j denoting the pixel row and column, respectively. In addition to using the full number of image pixels for calculating the correlation coefficient, a binning method is also used in which pixels are binned into subsets and then Equation 24 is computed. The effect of binning is to increase the similarity between images as binning smooths out random speckle fluctuations.

From measurements of optimized patterns as a function of time it's determined that in the absence of tampering the full resolution correlation coefficient remains >0.5 over several days, while the subset correlation coefficient is >0.8 for the same time frame. Therefore these values are used as the tamper indication thresholds. For values greater than the threshold, it is uncertain whether tampering has occurred or whether the change is due to drift in the experimental system.

To systematically test the tamper indicating abilities of the surface markers the following procedure was used for tamper testing:

1. The surface marker is applied to a stable surface and allowed to fully cure.
2. Using the reflectance based optical setup the surface marker's optical signature is measured, with both the optimal wavefront and marker's optical response being recorded.
3. The surface marker is then tampered with using one of the following methods:
   (a) Poking and prodding,
   (b) Heating using a heat gun,
   (c) Applying solvents,
   (d) Removal using a knife, then replacement,
   (e) Removal using a heat gun, then replacement, and
   (f) Removal using any method followed by substitution of new surface marker.
4. The tampered sample is then interrogated with the optimal wavefront and its optical response is measured.
5. The new optical response is compared to the initial response using either full resolution correlation or subset correlation.
6. The procedure is repeated five times for each tampering method and the resulting correlation coefficients are averaged to determine a mean value and uncertainty.

Results and Discussion

The first set of tampering attacks performed on the surface markers are mechanical attacks including: poking on the optical axis, poking off the optical axis, partial delamination, and full delamination. For the delamination attacks a razor blade was used to either peel off a corner of the surface marker or to fully peel the surface marker off the substrate. Once removed the surface marker was replaced to simulate an attacker removing the nanocomposite and replacing it. The correlation coefficient results of the various mechanical tampering tests are compiled in Table VII.

TABLE VII

Subset and full resolution correlation coefficients resulting from different tampering methods used on each polymer type. The correlation coefficient threshold value for indicating tampering is 0.8 for full resolution calculation and 0.5 for subset resolution.

| Test | Flexible PU | | Rigid PU | |
|---|---|---|---|---|
| | Full Res. | Subset (bin 15) | Full Res. | Subset (bin 15) |
| Off Axis Poking | 0.69 ± 0.20 | 0.960 ± 0.0040 | 0.21 ± 0.12 | 0.385 ± 0.084 |
| On Axis Poking | 0.55 ± 0.10 | 0.950 ± 0.050 | 0.050 ± 0.024 | 0.527 ± 0.090 |
| Partial Delamination | 0.350 ± 0.080 | 0.75 ± 0.18 | 0.0248 ± 0.0021 | 0.293 ± 0.010 |
| Full Delamination | 0.018 ± 0.010 | 0.037 ± 0.012 | −0.0088 ± 0.0050 | −0.036 ± 0.010 |

From Table VII it's found that the surface marker based on the rigid PU indicates tampering for all mechanical attacks, while the flexible PU based surface marker only indicates tampering for the delamination attacks. The failure of the flexible PU surface marker to indicate tampering for poking attacks can be attributed to the system's elastic response to deformation.

While different results are obtained for the two polymers with regards to poking, both clearly indicate tampering for partial and full delamination, with the correlation coefficients being on the order of $10^{-2}$ for full removal and replacement. The strong response to full removal and replacement is due to the positional sensitivity of the wavefront-sample coupling as it is practically impossible to replace the surface marker perfectly. Additionally, as evidenced by the partial delamination tests, the optimal wavefront and sample are decoupled by the deformations involved in delaminating the surface marker.

Next, the surface markers' response to thermal attacks was tested using a forced air heat gun to heat up the sample with the intended purpose of delamination and replacement. However, even after several minutes of heating, the samples were still firmly attached and a razor blade was still required to remove the samples. This implies a strong resistance to thermal removal of the samples. While it was not possible to simply remove the samples using heat as planned, an unintended result of these thermal tests is the observation of the correlation coefficient depending on the sample temperature.

To better understand the influence of temperature on the correlation coefficient heating measurements were performed in which the reflected pattern was continuously imaged during direct heating of the sample followed by a period of cooling. The temperature of the substrate was also measured during this process using a K-Type thermocouple. Once the imaging measurements are completed they're used to calculate the correlation coefficient as a function of time during heating, which is shown in FIG. 12 along with the substrate heating profile.

Figure 12:
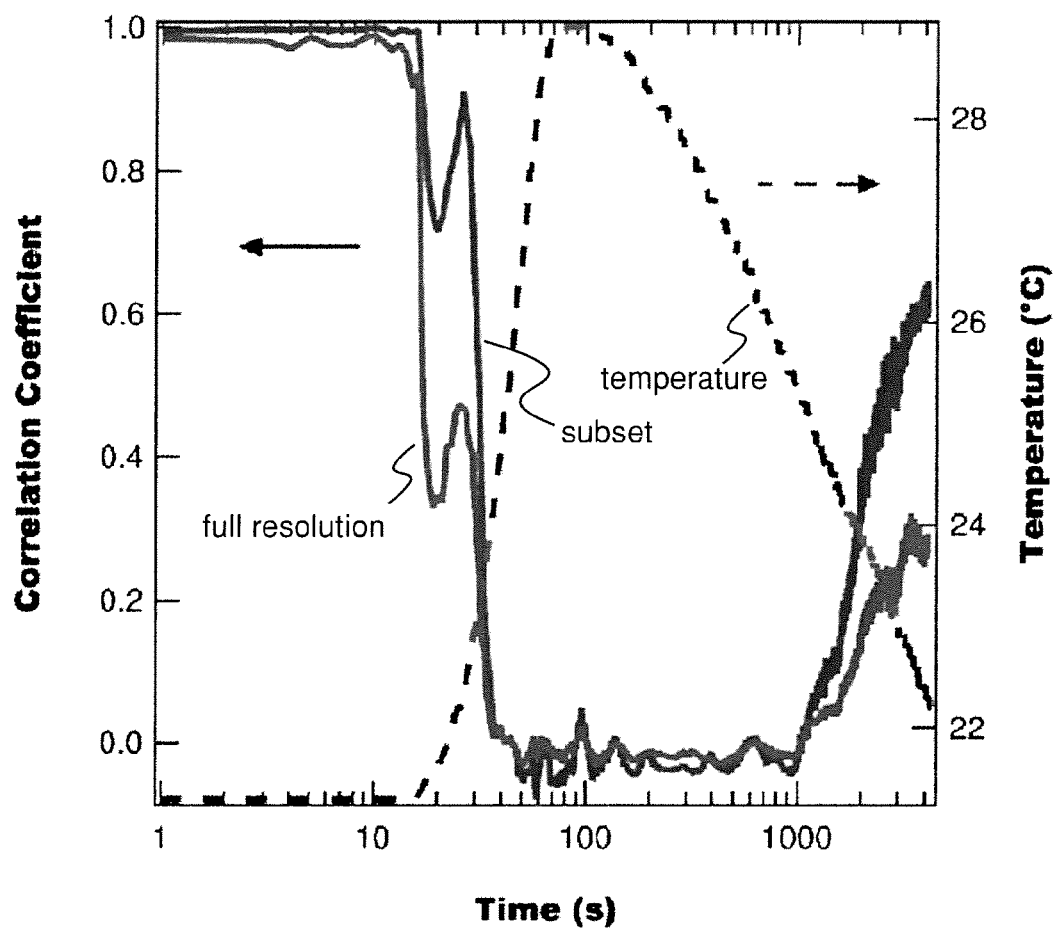
FIG. 12 shows correlation coefficient and substrate temperature as a function of time. As the sample is heated the wavefront-sample coupling is quickly broken. After the heat source is turned off and the sample cools the correlation coefficient is found to partially recover.

From FIG. 12 it's found that as the heat source is turned on and the temperature begins to rise, the correlation factor quickly drops as the optimal wavefront and sample become decoupled due to heating. While this decoupling is found to be complete (with the correlation factor dropping to $\approx -10^{-2}$) it is found to be partially reversible, as the subset correlation returns to 0.63 and full resolution correlation returns to 0.30 as the sample cools. Based on these observations it's concluded that decoupling during heating occurs due to two main mechanisms: (1) thermal expansion of the polymer host and (2) the temperature dependence of the refractive index of both the NPs and polymer host. When the sample is heated it expands and the refractive indices of the two materials change. This leads to the reflection eigenchannels changing (as they depend on both the index mismatch and sample size) thus making the incident wavefront no longer optimally shaped. Once heat is removed and the sample cools, it returns to it's initial size and refractive index mismatch leading to the correlation coefficient increasing. However, since thermal expansion of a disordered media is an irreversible process the correlation coefficient does not fully recover.

As a further note respecting FIG. 12, based on comparing the temporal profiles of the heating curve and correlation curves, the temperature dependence is interpreted to be such that a change of only 4° C. results in full decoupling. This could require the temperature to be maintained within a small margin for certain embodiments. However, this interpretation is based on this particular experimental setup and is not necessarily universally required. The measured temperature in FIG. 12 is the temperature of the substrate, which is heated indirectly through the PUF. While the substrate temperature only rises by 4° C. for full decoupling, the sample is actually heated to a greater degree.

The final tampering method tested is with solvents in an attempt to remove the PUFs without physical deformation to the PUF. For this purpose three different solvents were tested: methanol, proponal, and acetone. For all three solvents it was found that the PUFs remain firmly attached to the substrate with the solvents having no influence on their attachment. Due to the resilience of the PUFs against mild solvents more potent solvents (Hexane, Toluene, Dichloromethane, etc.) were also considered. However, these solvents tend to dissolve the PUFs, which is a clear indication of tampering.

While the application of mild solvents fails to affect the PUFs' attachment to the substrate, mild solvents still dynamically affect the wavefront sample coupling. FIGS. 13A-13F show the correlation coefficient as a function of time for each solvent and both PU types, with the different solvents and PU types found to produce drastically different results. From FIGS. 13A-13F the PUF response to the application of solvent is classified into two categories: temporary decoupling and permanent decoupling. Temporary decoupling consists of the correlation coefficient dropping to near zero shortly after application and then a short time later the correlation coefficient returns to a value above the tamper-indication threshold. In the case of permanent decoupling the correlation coefficient drops to near zero after solvent application and then remains below the tampering indication threshold such that tampering is still indicated at a much later time.

In the temporary decoupling category, there are the rigid PU responses to acetone (FIG. 13E) and propanol (FIG. 13F) as well as the flexible PU response to propanol (FIG. 13C). In all three cases, within one to two minutes the correlation coefficient returns to a value at (or above) the tamper indication threshold, albeit with some decoherence effects occurring after a long time, which occur even in the absence of tampering. These results mean that for these solvent-PUF combinations no indication of tampering would be expected in a field application.

In the category of permanent decoupling, there are the responses of the flexible PU to methanol (FIG. 13A) and acetone (FIG. 13B) as well as the response of the rigid PU to methanol (FIG. 13D). For all three solvent-PUF combinations tampering is indicated by the correlation coefficient long after the solvent was applied. This is an ideal behavior for a tamper indicating seal.

Based on these results, it's concluded that the flexible PU is sensitive to both methanol and acetone, while the rigid PU is only sensitive to methanol. Both PUs are insensitive to propanol.

Thus far in this tamper indication section, tampering attacks have been considered in which a seal is tampered with and either left in position or removed and replaced. Another form of tampering is the complete removal of a seal and its replacement with a counterfeit seal or mimicking system. To better understand what would be involved in such a procedure, the underlying physics behind optimization are considered. For an electric field $E_b$ incident on a disordered system, with reflection matrix $r_{ab}$ (where a are incident channels and b are reflected channels), the reflected electric field is Equation 25, $$E_a = \sum_b^N r_{ab} E_b. \quad (25)$$

Wavefront-shaping based optimization seeks to optimize the reflected field $E_a$, by optimally shaping the incident filed $E_b$. Assuming plane waves with phase-only wavefront modulation the optimal incoming electric field is given by Equation 26:

$$E_b^{opt} = \frac{1}{\sqrt{N}} \exp\{-i \arg(r_{ab})\}. \quad (26)$$

From Equation 26 it's seen that the key quantity that needs to be cloned in order to fool authentication is the reflection matrix $r_{ab}$.

Figure 14:
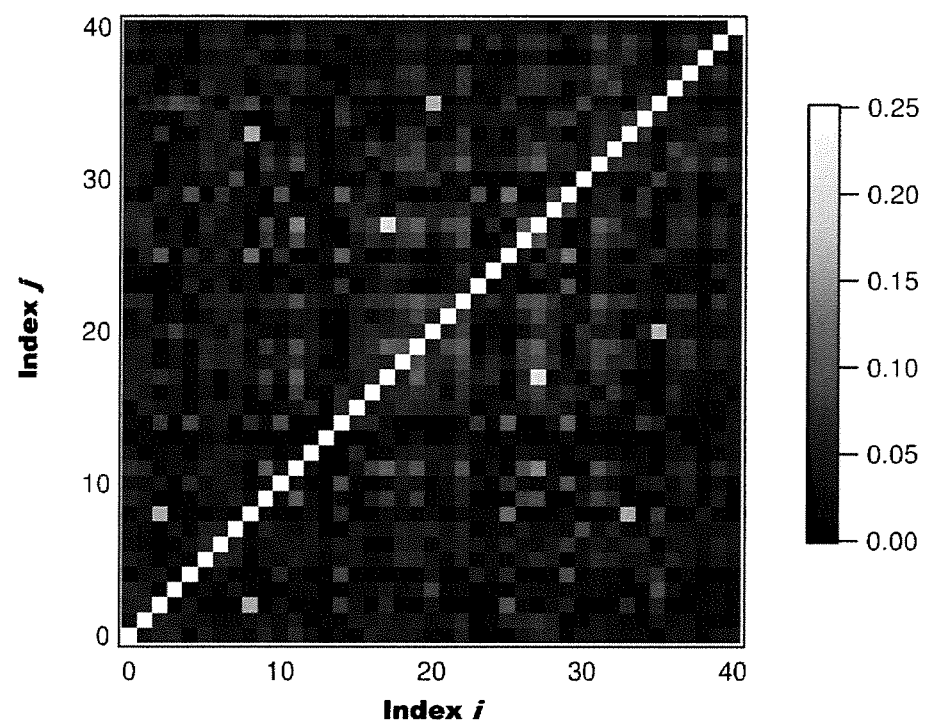
FIG. 14 shows a speckle correlation matrix for patterns measured at forty different positions on the same sample.

To get a better grasp on the complexity of the reflection matrix and to demonstrate the sensitivity of the reflection matrix to the specific realization of disorder, the speckle patterns produced from a single sample probed at forty different locations using a flat wavefront are measured. The speckle pattern measured in this way is directly related to the reflection matrix (from Equation 25) and therefore provides the ability to compare the reflection matrices at the forty different locations. Once the speckle patterns are recorded they are compared to each other using Pearson's correlation coefficient. A correlation matrix $c_{ij}$ is produced where i;j are indices denoting the forty different locations with $c_{ii}=1$. FIG. 14 shows a two-dimensional representation of the correlation matrix for different indices. From FIG. 14 it's found that for i≠j the correlation between speckle patterns is small, implying that the reflection matrices are uncorrelated. To quantify how correlated the reflection matrices are, a histogram of non-unity values was generated from the correlation matrix with the result shown in FIG. 15. From FIG. 15 we find that the correlation coefficients are Gaussian distributed with a mean value of $c_0=4.174(\pm 0.078)\times 10^{-2}$. This implies that there is a small degree of correlation between points, as the average correlation is expected to be zero for completely uncorrelated matrices.

Figure 15:
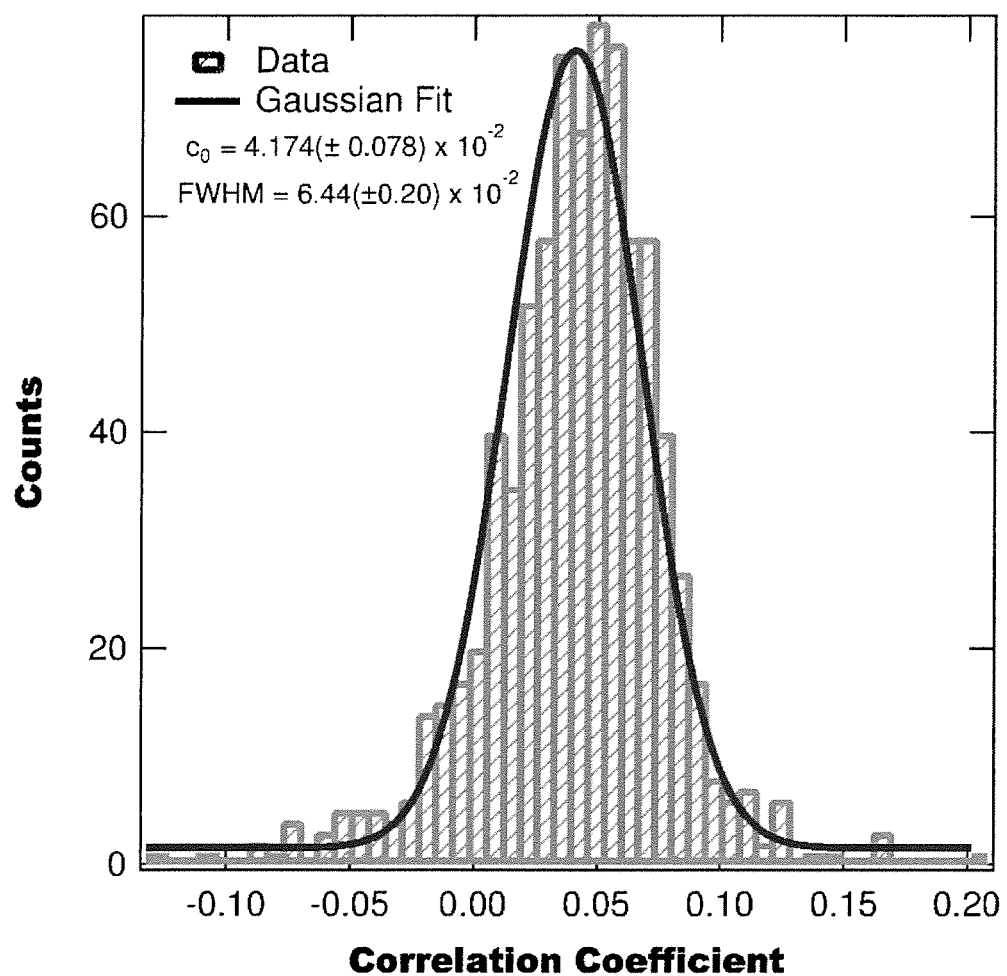
FIG. 15 shows a histogram of correlation values from the correlation matrix shown in FIG. 14. The correlation coefficients are Gaussian distributed with a non-zero mean which implies a small degree of correlation.

The physical interpretation of FIGS. 14 and 15 is that the reflection matrices depend strongly on the specific realization of disorder and not merely on the macroscopic average parameters. Additionally, the nonzero mean correlation can be interpreted as a measure of long range correlations predicted for scattering materials. On the practical side, these results imply that an attacker cannot merely remove the surface marker and replace it with a macroscopically identical material, as the microscopic distribution will not be the same. Therefore to clone the surface marker an attacker will need to have advanced technology to precisely move nanoparticles in a polymer matrix as well as possess the ability to know either: (a) the precise distribution of scattering particles or (b) an alternative distribution which produces the identical reflection matrix. Currently these tasks are technically unfeasible; therefore it's acceptable to describe the materials and markers described herein as currently "unclonable".

While precise cloning is currently unfeasible, a far more likely strategy is a mimicking attack in which a different system is used in order to produce the same reflection matrix while never actually reproducing the actual surface marker. Currently, the simplest method to produce such a mimic is to use the known optimal wavefront (or measure the reflection matrix of the surface marker) and write a corresponding hologram. While such an attack cannot be detected solely by the wavefront authentication method, it will most likely be obvious if a visual inspection is performed. Also, as added safeguards against such attacks the sensitive information involved (optimal wavefront), probed area of sample, original sample response, etc.) should be secured with proper security measures.

Table VIII lists whether tampering is indicated for a specific polymer and tamper test, with "y" meaning that tampering is indicated and "n" meaning that tampering is not indicated. From Table VIII it's shown that the rigid PU indicated tampering in all mechanical and thermal attacks, and in most solvent attacks. With regards to the flexible PU, from Table VII it's shown that the flexible PU fails to indicate tampering for the poking attacks, with the mechanism related to the elasticity of the material. However, while the flexible PU performed poorly for the poking attacks, it successfully indicated tampering for the delamination attacks, thermal attacks, and solvent attacks.

TABLE VIII

Tamper indication summary.

| | Flexible PU | | Rigid PU | |
| --- | --- | --- | --- | --- |
| Test | Full Res. | Subset (bin 15) | Full Res. | Subset (bin 15) |
| Off Axis Poking | n | n | y | y |
| On Axis Poking | n | n | y | y |
| Partial Delamination | y | y | y | y |
| Full Delamination | y | y | y | y |
| Heating | y | y | y | y |
| Methanol | y | y | y | y |
| Acetone | y | y | y | n |
| Propanol | y | y | n | n |

While these tamper tests are only a subset of possible attacks on a tamper indicating seal, they provide encouraging evidence for both the flexible and rigid PU as useful host materials in the implementation of O-PUFs. To inhibit or prevent tampering attacks on the SLM characterization system, additional security protocols and measures may be included in some embodiments such as physical barriers (locking equipment, video surveillance, etc.), software barriers (passwords, firewalls, etc.) and personnel requirements (proper training, background checks, etc.).

It is to be understood that features described with regard to the various embodiments herein may be mixed and matched in any combination without departing from the spirit and scope of the invention. Although different selected embodiments have been illustrated and described in detail, it is to be appreciated that they are exemplary, and that a variety of substitutions and alterations are possible without departing from the spirit and scope of the present invention.

We claim:

1. An authentication system, comprising:
   an optical source of radiation;
   a spatial light modulator (SLM) configured to modulate a wavefront of the optical source of radiation;
   one or more optical components configured to use the modulated wavefront so as to provide an optical source of radiation challenge to at least one of:
      the surface of a sample and
      within a desired volume in the bulk of the sample;
   a detector configured to analyze an induced optical response by the sample as a result of being illuminated with the optical source of radiation challenge; and
   a controller coupled to the SLM and configured to cooperatively operate on a closed feedback loop to optimize the induced optical response detected by the detector by varying in an iterative manner, one or more system parameters selected from: an SLM bin size (b), a number of SLM phase steps (M), an active SLM area ($L^2$), a detector integration radius (r), and an on-sample beam spot size (w), while holding all other of the parameters fixed so as to optimize the authentication system for subsequent measurements of the intensity enhancement or optical pattern of the induced optical response by the surface marker.

2. The authentication system of claim 1, wherein the authentication system is configured in at least one authenticating geometry selected from: a reflectance geometry, a transmission geometry, a fluorescence geometry, a random lasing (RL) geometry, a nonlinear optics geometry, a magneto-optics geometry, a mechano-optics geometry, an electro-optics geometry, and a thermo-optics geometry.

3. The authentication system of claim 2, wherein the authenticating geometry is a Quantum Secure Authentication (QSA) geometry.

4. The authentication system of claim 1, further comprising the sample, wherein the sample comprises an optically scattering composite.

5. The authentication system of claim 4, wherein the scattering composite is at least one scattering composite selected from: a polymer matrix containing inorganic particles; a polymer matrix containing organic particles; a polymer matrix containing inorganic and organic particles; a polymer matrix containing inorganic particles and optically-active molecules; a polymer matrix containing organic particles and optically-active molecules; a polymer matrix containing inorganic and organic particles and optically-active molecules.

6. The authentication system of claim 5, wherein the polymer matrix comprises at least one of: a polyurethane and an epoxy-based material.

7. The authentication system of claim 5, wherein the inorganic particles comprises at least one material selected from: $ZrO_2$, $TiO_2$, and $Y_2O_3$.

8. The authentication system of claim 5, wherein the organic particles comprises at least one material selected from: sucrose, acetaminophen, anthracene, and tetracene.

9. The authentication system of claim 5, wherein the optically-active molecules comprises at least one light-emitting and/or light-absorbing molecules selected from: Rhodamines, Coumarines, Anthraquinones, Exalites, and lanthanide-containing dyads.

10. The authentication system of claim 1, further comprising the sample, wherein the sample comprises at least one of: a manufactured hardware component, a semi-conductor component, a packaging material, a circuit design map, a populated circuit board, a packaged chip, and a pre-packaged component.

11. The authentication system of claim 1, further comprising the sample and a secured item, wherein the sample configured to receive an optical source of radiation challenge is additionally coupled to the secured item, wherein the induced optical response indicates the authentication of the secured item.

12. The authentication system of claim 11, wherein the secured item comprises at least one of: a system(s), a site(s), a container, a manufactured hardware component, a semi-conductor component, a packaging material, a circuit design map, a populated circuit board, a packaged chip, and a pre-packaged component.

13. The authentication system of claim 1, wherein the detector is at least one detector selected from: a photodiode, avalanche photodiode, photomultiplier tube (PMT), a Charge Coupled Device (CCD), a complementary metal-oxide-semiconductor (CMOS) array, a Charge Injection Device (CID) detector, an avalanche CCD photo-detector, area sensors with an image intensifier, and an EMCCD Electron Multiplying CCD (EMCCD).

14. The authentication system of claim 1, wherein the SLM is at least one electrically-addressed or optically-addressed device selected from: a liquid crystal on silicon (LCOS) device and a digital micro-mirror (DMD) device.

15. The authentication system of claim 1, wherein the authentication system is configured to authenticate remotely or onsite.

16. The authentication system of claim 1, wherein the optical source of radiation comprises at least one of: a diode laser, a Diode pumped Solid State lasers (DPSS) laser, a frequency doubled laser, a frequency tripled laser, a quadrupled diode lasers, a superluminescent LED, a solid-state laser, an optical parametric oscillator (OPO), and a gas lasers.

17. An authentication method, comprising:
   modulating a wavefront of an optical source of radiation;
   utilizing the modulated wavefront to provide an optical source of radiation challenge to at least one of:
      the surface of a sample and
      the volume in the bulk of the sample so as to induce an optical response;
   monitoring the induced optical response from the sample;
   optimizing the authentication process by varying in an iterative manner, one or more system parameters selected from: an SLM bin size (b), a number of SLM phase steps (M), an active SLM area ($L^2$), a detector integration radius (r), and an on-sample beam spot size (w), while holding all other of the parameters fixed; and analyzing and optimizing the induced optical response from the sample as a result of being illuminated with the optical source of radiation challenge.

* * * * *